United States Patent
Pantaleo et al.

(10) Patent No.: US 11,130,807 B2
(45) Date of Patent: *Sep. 28, 2021

(54) IMMUNOLOGICAL REAGENTS

(71) Applicant: MabQuest SA, Pully (CH)

(72) Inventors: Giuseppe Pantaleo, Pully (CH); Craig Fenwick, Lausanne (CH)

(73) Assignee: MabQuest, S.A., Pully (CH)

( * ) Notice: Subject to any disclaimer, the term of this patent is extended or adjusted under 35 U.S.C. 154(b) by 230 days.

This patent is subject to a terminal disclaimer.

(21) Appl. No.: 15/981,977

(22) Filed: May 17, 2018

(65) Prior Publication Data

US 2019/0106493 A1    Apr. 11, 2019

Related U.S. Application Data

(63) Continuation of application No. 15/329,760, filed as application No. PCT/IB2015/055943 on Aug. 5, 2015, now Pat. No. 9,982,053.

(60) Provisional application No. 62/093,368, filed on Dec. 17, 2014, provisional application No. 62/053,366, filed on Sep. 22, 2014, provisional application No. 62/033,177, filed on Aug. 5, 2014.

(51) Int. Cl.
*C07K 16/28* (2006.01)
*A61K 39/00* (2006.01)
*C07K 16/10* (2006.01)
*G01N 33/68* (2006.01)

(52) U.S. Cl.
CPC ...... *C07K 16/2818* (2013.01); *C07K 16/1063* (2013.01); *G01N 33/6893* (2013.01); *A61K 2039/507* (2013.01); *C07K 2317/21* (2013.01); *C07K 2317/24* (2013.01); *C07K 2317/31* (2013.01); *C07K 2317/565* (2013.01); *C07K 2317/74* (2013.01); *C07K 2317/75* (2013.01); *C07K 2317/76* (2013.01); *C07K 2317/92* (2013.01)

(58) Field of Classification Search
CPC .......... C07K 2317/76; A61K 2039/507; A61K 47/6849; A61K 47/6851
See application file for complete search history.

(56) References Cited

U.S. PATENT DOCUMENTS

| | | |
|---|---|---|
| 4,816,567 A | 3/1989 | Cabilly et al. |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,629,204 A | 5/1997 | Honjo et al. |
| 5,633,425 A | 5/1997 | Lonberg et al. |
| 5,661,016 A | 8/1997 | Lonberg et al. |
| 5,693,761 A | 12/1997 | Queen et al. |
| 5,698,520 A | 12/1997 | Alakhov et al. |
| 6,407,213 B1 | 6/2002 | Carter |
| 6,808,710 B1 | 10/2004 | Wood et al. |
| 7,101,550 B2 | 9/2006 | Wood et al. |
| 7,488,802 B2 | 2/2009 | Collins et al. |
| 7,521,051 B2 | 4/2009 | Collins et al. |
| 7,563,869 B2 | 7/2009 | Honjo et al. |
| 7,595,048 B2 | 9/2009 | Honjo et al. |
| 7,638,492 B2 | 12/2009 | Wood et al. |
| 7,858,746 B2 | 12/2010 | Honjo et al. |
| 8,008,449 B2 | 8/2011 | Korman et al. |
| 8,168,179 B2 | 5/2012 | Honjo et al. |
| 8,168,757 B2 | 5/2012 | Finnefrock et al. |
| 8,287,856 B2 | 10/2012 | Li et al. |
| 8,354,509 B2 | 1/2013 | Carven et al. |
| 8,552,154 B2 | 10/2013 | Freeman et al. |
| 8,652,465 B2 | 2/2014 | Freeman et al. |
| 8,728,474 B2 | 5/2014 | Honjo et al. |
| 8,735,553 B1 | 5/2014 | Li et al. |
| 8,741,295 B2 | 6/2014 | Olive |
| 8,829,165 B2 | 9/2014 | Jackson et al. |
| 8,900,587 B2 | 12/2014 | Carven et al. |
| 8,927,697 B2 | 1/2015 | Davis et al. |
| 8,952,136 B2 | 2/2015 | Carven et al. |
| 8,993,731 B2 | 3/2015 | Tyson |
| 9,029,315 B2 | 5/2015 | Chen et al. |
| 9,067,999 B1 | 6/2015 | Honjo et al. |
| 9,073,994 B2 | 7/2015 | Honjo et al. |
| 9,090,994 B2 | 7/2015 | Zhang et al. |
| 9,102,728 B2 | 8/2015 | Tyson |
| 9,163,087 B2 | 10/2015 | Kuchroo et al. |
| 9,205,148 B2 | 12/2015 | Langermann et al. |
| 9,220,776 B2 | 12/2015 | Sharma et al. |
| 9,402,899 B2 | 8/2016 | Honjo et al. |
| 9,982,052 B2 * | 5/2018 | Pantaleo ............ G01N 33/6893 |
| 9,982,053 B2 * | 5/2018 | Pantaleo ................. A61P 31/18 |
| 10,294,299 B2 * | 5/2019 | Pantaleo ................. A61P 31/18 |
| 2002/0160000 A1 | 10/2002 | Wood et al. |
| 2004/0209243 A1 | 10/2004 | Nixon et al. |
| 2004/0213795 A1 | 10/2004 | Collins et al. |
| 2009/0217401 A1 | 8/2009 | Korman et al. |
| 2010/0028330 A1 | 2/2010 | Collins et al. |
| 2010/0040614 A1 | 2/2010 | Ahmed et al. |

(Continued)

FOREIGN PATENT DOCUMENTS

| | | |
|---|---|---|
| JP | 05-336973 | 6/1992 |
| WO | 9428933 A1 | 12/1994 |
| WO | 2013169693 A1 | 11/2013 |

OTHER PUBLICATIONS

Ghiotto et al., PD-L1 and PD-L2 differ in their molecular mechanisms of interaction with PD-1. Int Immunol. Aug. 2010; 22(8): 651-660 (Year: 2010).*

(Continued)

*Primary Examiner* — Brad Duffy
*Assistant Examiner* — Cheom-Gil Cheong
(74) *Attorney, Agent, or Firm* — Patrick J. Halloran

(57) ABSTRACT

This disclosure relates to binding agents with specificity for programmed cell death 1 (PD-1) and to methods for using the same to treat, prevent and/or ameliorate an infectious disease (e.g., human immunodeficiency virus (HIV)), cancer and/or autoimmunity.

9 Claims, 9 Drawing Sheets

Specification includes a Sequence Listing.

(56) References Cited

U.S. PATENT DOCUMENTS

| | | |
|---|---|---|
| 2011/0081341 A1 | 4/2011 | Honjo et al. |
| 2011/0171215 A1 | 7/2011 | Davis et al. |
| 2011/0229461 A1 | 9/2011 | Tyson |
| 2012/0039906 A1 | 2/2012 | Olive |
| 2013/0071403 A1 | 3/2013 | Rolland et al. |
| 2013/0202623 A1 | 8/2013 | Chomont et al. |
| 2014/0044738 A1 | 2/2014 | Langermann et al. |
| 2014/0341902 A1 | 11/2014 | Maecker et al. |
| 2015/0203579 A1 | 7/2015 | Papadopoulos et al. |
| 2015/0290316 A1 | 10/2015 | Graziano et al. |
| 2016/0075783 A1 | 3/2016 | King et al. |
| 2016/0251436 A1 | 9/2016 | Amirina et al. |
| 2016/0272708 A1 | 9/2016 | Chen |
| 2016/0319019 A1 | 11/2016 | Amirina et al. |

OTHER PUBLICATIONS

Wei, F., et al., "Strength of PD-1 signaling differentially affects T-cell effector functions," Proc Natl Acad Sci U S A, 2013. 110(27): p. E2480-9.
Wherry, E.J. and M. Kurachi, "Molecular and cellular insights into T cell exhaustion," Nat Rev Immunol, 2015. 15 (8): p. 486-99.
Winograd, R., et al., "Induction of T-cell Immunity Overcomes Complete Resistance to PD-1 and CTLA-4 Blockade and Improves Survival in Pancreatic Carcinoma," Cancer Immunol Res, 2015. 3(4): p. 399-411.
Zak, K.M., et al., "Structure of the Complex of Human Programmed Death 1, PD-1, and Its Ligand PD-L1," Structure, 2015. 23(12): p. 2341-8.
Zhang, J.Y., et al., "PD-1 up-regulation is correlated with HIV-specific memory CD8+ T-cell exhaustion in typical progressors but not in long-term nonprogressors," Blood, 2007. 109(11): p. 4671-8.
Zhang, X., et al., "Structural and functional analysis of the costimulatory receptor programmed death-1," Immunity, 2004. 20(3): p. 337-47.
CD279 (PD-1) Monoclonal Antibody (J116), Functional Grade, eBioscienceTM. https://www.thermofisher.com/antibody/product/CD279-PD-1-Antibody-clone-J116-Monoclonal/16/9989-82.
Alvarez, I.B., et al., "Role played by the programmed death-1-programmed death ligand pathway during innate immunity against *Mycobacterium tuberculosis*," J Infect Dis, 2010. 202(4): p. 524-32.
Ansell, S.M., et al., "PD-1 blockade with nivolumab in relapsed or refractory Hodgkin's lymphoma," N Engl J Med, 2015. 372(4): p. 311-9.
Baitsch, L., et al., "Exhaustion of tumor-specific CD8(+) T cells in metastases from melanoma patients," J Clin Invest, 2011. 121(6): p. 2350-60.
Barber, D.L., et al., "Restoring function in exhausted CD8 T cells during chronic viral infection," Nature, 2006. 439 (7077): p. 682-687.
Blackburn, S.D., et al., "Tissue-specific differences in PD-1 and PD-L1 expression during chronic viral infection: implications for CD8 T-cell exhaustion," J Virol, 2010. 84(4): p. 2078-2089.
Blackburn, S.D., et al., "Coregulation of CD8+ T cell exhaustion by multiple inhibitory receptors during chronic viral infection," Nat Immunol, 2009. 10(1): p. 29-37.
Brown, K.E., et al., "Role of PD-1 in regulating acute infections," Curr Opin Immunol, 2010. 22(3): p. 397-401.
Carbognin, L., et al., "Differential Activity of Nivolumab, Pembrolizumab and MPDL3280A according to the Tumor Expression of Programmed Death-Ligand-1 (PD-L1): Sensitivity Analysis of Trials in Melanoma, Lung and Genitourinary Cancers," PLoS One, 2015. 10(6): p. e0130142.
Cheng, X., et al., "Structure and interactions of the human programmed cell death 1 receptor," J Biol Chem, 2013. 288(17): p. 11771-85.
Chinai, J.M., et al., "New immunotherapies targeting the PD-1 pathway," Trends Pharmacol Sci, 2015. 36(9): p. 587-95.

Day, C.L., et al., "PD-1 expression on HIV-specific T cells is associated with T-cell exhaustion and disease progression," Nature, 2006. 443(7109): p. 350-4.
Drake, C.G., E.J. Lipson, and J.R. Brahmer, "Breathing new life into immunotherapy: review of melanoma, lung and kidney cancer," Nat Rev Clin Oncol, 2014. 11(1): p. 24-37.
Driessens, G., J. Kline, and T.F. Gajewski, "Costimulatory and coinhibitory receptors in anti-tumor immunity," Immunol Rev, 2009. 229(1): p. 126-44.
Freeman, G.J., et al., "Reinvigorating exhausted HIV-specific T cells via PD-1-PD-1 ligand blockade," J Exp Med, 2006. 203(10): p. 2223-7.
Garon, E.B., et al., "Pembrolizumab for the treatment of non-small-cell lung cancer," N Engl J Med, 2015. 372(21): p. 2018-28.
Goldberg, M.V., et al., "Role of PD-1 and its ligand, B7-H1, in early fate decisions of CD8 T cells," Blood, 2007. 110 (1): p. 186-92.
Ha, S.J. et al., "Enhancing therapeutic vaccination by blocking PD-1-mediated inhibitory signals during chronic infection," J Exp Med, 2008. 205(3): p. 543-55.
Hamid, O., et al., "Safety and tumor responses with lambrolizumab (anti-PD-1) in melanoma," N Engl J Med, 2013. 369(2): p. 134-44.
Herati, R.S., et al., "Circulating CXCR5+PD-1+ response predicts influenza vaccine antibody responses in young adults but not elderly adults," J Immunol, 2014. 193(7): p. 3528-37.
Huang, R.Y., et al., "LAG3 and PD1 co-inhibitory molecules collaborate to limit CD8+ T cell signaling and dampen antitumor immunity in a murine ovarian cancer model," Oncotarget, 2015. 6(29): p. 27359-77.
Kao, C., et al., "Transcription factor T-bet represses expression of the inhibitory receptor PD-1 and sustains virus-specific CD8+ T cell responses during chronic infection," Nat Immunol, 2011. 12(7): p. 663-71.
Larkin, J., et al., "Combined Nivolumab and Ipilimumab or Monotherapy in Untreated Melanoma," N Engl J Med, 2015. 373(1): p. 23-34.
Lazar-Molnar, E., et al., "Crystal structure of the complex between programmed death-1 (PD-1) and its ligand Pd-L2," Proc Natl Acad Sci U S A, 2008. 105(30): p. 10483-8.
Lin, D.Y., et al., "The PD-1/PD-L1 complex resembles the antigen-binding Fv domains of antibodies and T cell receptors," Proc Natl Acad Sci U S A, 2008. 105(8): p. 3011-6.
Maier, H., et al., "PD-1:PD-L1 interactions contribute to the functional suppression of virus-specific CD8+ T cell lymphocytes in the liver," J Immunol, 2007. 178(5): p. 2714-20.
Mellman, L, G. Coukos, and G. Dranoff, "Cancer immunotherapy comes of age," Nature, 2011. 480(7378): p. 180-9.
Nakamoto, N., et al., "Functional restoration of HCV-specific CD8 T cells by PD-1 blockade is defined by PD-1 expression and compartmentalization," Gastroenterology, 2008. 134(7): p. 1927-37, 1937 e1-2.
Palucka, A.K. and L.M. Coussens, "The Basis of Oncoimmunology," Cell, 2016. 164(6): p. 1233-47.
Pardoll, D.M., "The blockade of immune checkpoints in cancer immunotherapy," Nat Rev Cancer, 2012. 12(4): p. 252-64.
Parry, R.V., et al., "CTLA-4 and PD-1 receptors inhibit T-cell activation by distinct mechanisms," Mol Cell Biol, 2005. 25(21): p. 9543-53.
Patnaik, A., et al., "Phase I Study of Pembrolizumab (MK-3475; Anti-PD-1 Monoclonal Antibody) in Patients with Advanced Solid Tumors," Clin Cancer Res, 2015. 21(19): p. 4286-93.
Patsoukis, N., et al., "Selective effects of PD-1 on Akt and Ras pathways regulate molecular components of the cell aycle and inhibit T cell proliferation," Sci Signal, 2012. 5(230): p. ra46.
Pauken, K.E. and E.J. Wherry, "Overcoming T cell exhaustion in infection and cancer," Trends Immunol, 2015. 36(4): p. 265-76.
Petrovas, C., et al., "PD-1 is a regulator of virus-specific CD8+ T cell survival in HIV infection," J Exp Med, 2006. 203(10): p. 2281-92.
Quigley, M., et al., "Transcriptional analysis of HIV-specific CD8+ T cells shows that PD-1 inhibits T cell function by upregulating BATF," Nat Med, 2010. 16(10): p. 1147-51.
Riley, J.L., "PD-1 signaling in primary T cells," Immunol Rev, 2009. 229(1): p. 114-25.

(56) References Cited

OTHER PUBLICATIONS

Rizvi, N.A., et al., "Activity and safety of nivolumab, an anti-PD-1 immune checkpoint inhibitor, for patients with advanced, refractory squamous non-small-cell lung cancer (CheckMate 063): a phase 2, single-arm trial," Lancet Oncol, 2015. 16(3): p. 257-65.
Robert, C., et al., "Pembrolizumab versus Ipilimumab in Advanced Melanoma," N Engl J Med, 2015. 372(26): p. 2521-32.
Rutigliano, J.A., et al., "Highly pathological influenza A virus infection is associated with augmented expression of PD-1 by functionally compromised virus-specific CD8+ T cells," J Virol, 2014. 88(3): p. 1636-51.
Sakthivel, P., M. Gereke, and D. Bruder, "Therapeutic intervention in cancer and chronic viral infections: antibody mediated manipulation of PD-1/PD-L1 interaction," Rev Recent Clin Trials, 2012. 7(1): p. 10-23.
Sharma, P. and J.P. Allison, "The future of immune checkpoint therapy," Science, 2015. 348(6230): p. 56-61.
Sheppard, K.A., et al., "Pd-1 inhibits T-cell receptor induced phosphorylation of the ZAP70/CD3zeta signalosome and downstream signaling to PKCtheta," FEBS Lett, 2004. 574(1-3): p. 37-41.
Soria, J.C., et al., "Immune checkpoint modulation for non-small cell lung cancer," Clin Cancer Res, 2015.21(10): p. 2256-62.
Swaika, A., W.A. Hammond, and R.W. Joseph, "Current state of anti-PD-L1 and anti-PD-1 agents in cancer therapy," Mol Immunol, 2015. 67(2 Pt A): p. 4-17.
Tan, M. and L. Quintal, "Pembrolizumab: a novel antiprogrammed death 1 (PD-1) monoclonal antibody for treatment of metastatic melanoma," J Clin Pharm Ther, 2015.
Tan, S., C.W.H. Zhang, and G.F. Gao, "Seeing is believing: anti-PD-1/PD-L1 monoclonal antibodies in action for aheckpoint blockade tumor immunotherapy," Signal Transduction and Targeted Therapy, 2016. 1: p. 16029.
Topalian, S.L., C.G. Drake, and D.M. Pardoll, "Immune checkpoint blockade: a common denominator approach to cancer therapy," Cancer Cell, 2015. 27(4): p. 450-61.
Topalian, S.L., et al., "Safety, activity, and immune correlates of anti-PD-1 antibody in cancer," N Engl J Med, 2012. 366(26): p. 2443-54.
Trautmann, L., et al., "Upregulation of PD-1 expression on HIV-specific CD8+ T cells leads to reversible immune dysfunction," Nat Med, 2006. 12(10): p. 1198-202.
Tumeh, P.C., et al., "PD-1 blockade induces responses by inhibiting adaptive immune resistance," Nature, 2014. 515 (7528): p. 568-71.
Affymetrix. CD279 (PD-1) Monoclonal Antibody, Functional Grade. Product No. 16/9989-80.
Agata, Y., et al., "Expression of the PD-1 antigen on the surface of stimulated mouse T and B lymphocytes", International Immunology, vol. 8, No. 5, Nov. 5, 1995, pp. 765-772.
Azvolinsky, A., "Another Anti-PD1 Immunotherapy Shows Promise for Melanoma Patients", CancerCommons, Nov. 25, 2013, 3 pages.
Barber, D.L., et al., "Restoring function in exhausted CD8 T cells during chronic viral infection." (Abstract), Nature, 439(7077), Dec. 28, 2005, pp. 682-687 (Abstract).
Batra, S.K., et al., "Isolation and Characterization of a Complementary DNA (PD-1) Differentially Expressed by Human Pancreatic Ductal Cell Tumors", Cell Growth & Differentiation, vol. 2, Aug. 1, 1991, pp. 385-390.
Biolegend, Inc., "Purified anti-human CD279 (PD-1) Antibody", www.biolegend.com, Dec. 30, 2013, 3 pages.
Blank C., et al., "Contribution of the PD-L1/PD-1 pathway to T-cell exhaustion: an update on implications for chronic nfections and tumor evasion.", Cancer Immunol Immunother, 56(5), Dec. 29, 2006, pp. 739-745.
Bristol-Myers Squibb Company, "Additional Survival Data on Nivolumab, an Investigational PD-1 Immune checkpoint Inhibitor, from Lung Cancer Cohort of a Phase 1 Study Presented at 15th World Conference on Lung Cancer", Business Wire NewsHQ, Oct. 25, 2013, 4 pages.

Da Silva, et al. Nivolumab: Anti-PD-1 monoclonal antibody cancer immunotherapy. Drugs of the Future. 39(1): 15-24 (2014).
Das, R et al. "Combination Therapy with Anti-CTLA-4 and Anti-PD-1 Leads to Distinct Immunologic Changes In Vivo", The Journal of Immunology, 194, Dec. 24, 2014, pp. 1-10.
Day, C., et al., "PD-1 expression on HIV-specific T cells is associated with T-cell exhaustion and disease progression", Nature, vol. 443, Sep. 21, 2006 , pp. 350-354.
Ebersbach, et al. Affilin-Novel Binding Molecules Based on Human y-B-Crystallin, an All β-Sheet Protein. J. Mol. Biol. 372 (1): 172-85 (Abstract) (2007).
Eichbaum, Q., "PD-1 signaling in HIV and chronic viral infection—potential for therapeutic intervention?" (Abstract), Curr Med Chem, 18(26), 2011 pp. 3971-3980 (Abstract).
Faghfuri, et al. Nivolumab and Pembrolizumab as Immune-Modulating Monoclonal Antibodies Targeting the PD-1 Receptor to Treat Melanoma. Expert Rev. Anticancer Ther., 15(9): 981-993 (2015).
Finnefrock, A.G., et al., "PD-1 Blockade in Rhesus Macaques: Impact on Chronic Infection and Prophylactic Vaccination", The Journal of Immunology, 182, 2009, pp. 980-987.
Freeman et al. Engagement of the PD-1 Immunoinhibitory Receptor by a Novel B7 Family Member Leads to Negative Regulation of Lymphocyte Activation. J. Exp. Med. 192(7): 1027-34 (2000).
Grabulovski, D., et al., "A Novel, Non-immunogenic Fyn SH3-derived Binding Protein with Tumor Vascular Targeting Properties", the Journal of Biological Chemistry, vol. 282, No. 5, Feb. 2, 2007, pp. 3196-3204.
Ha, S-J., et al., "Enhancing therapeutic vaccination by blocking PD-1-mediated inhibitory signals during chronic infection", The Journal of Experimental Medicine, vol. 205, No. 3, Mar. 17, 2008, pp. 543-555.
Haile, et al. Soluble CD80 Restores T Cell Activation and Overcomes Tumor Cell Programmed Cell Death Ligand 1-Mediated Immune Suppression. J. Immunol. 191(5): 2829-2836 (2013).
Hamid, et al. Safety and Tumor Responses with Lambrolizumab (Anti-PD-1) in Melanoma. N. Eng. J. Med. 369: 134-144 (2013).
Ingram, I., "FDA Approves Anti-PD-1 Drug for Advanced Melanoma", Cancer Network, Sep. 4, 2014, 1 page.
Ishida, Y., et al., "Induced expression of PD-1, a novel member of the immunoglobulin gene superfamily, upon programmed cell death", The EMBO Journal, vol. 11 No. 11, 1992, pp. 3887-3895.
Iwai, Y., et al., "Involvement of PD-L1 on tumor cells in the escape from host immune system and tumor immunotherapy by PD-L1 blockade", PNAS, vol. 99 No. 19, Sep. 17, 2002, pp. 12293-12297.
Iwai, Y., et al., "PD-1 Inhibits Antiviral Immunity at the Effector Phase in the Liver", The Journal of Experimental Medicine, vol. 198, No. 1, Jul. 7, 2003, pp. 39-50.
Katlama, C., et al., "Barriers to a cure for HIV: new ways to target and eradicate HIV-1 reservoirs", The Lancet , vol. 381 , Issue 9883 , Mar. 29, 2013, pp. 2109-2117.
Kaufmann, D.E., "The PD-1 Inhibitory Pathway in HIV Infection and the Potential for Therapeutic Intervention", DART 2010, Dec. 8, 2010, 19 pages.
Koide et al. Monobodies: antibody mimics based on the scaffold of the fibronectin type III domain. Methods Mol. Biol. 352, 95-109 (Abstract) (2007).
Kolata, G., "Breaking Through Cancer's Shield", The New York Times, Oct. 14, 2013 Oct. 14, 2013, 4 pages.
Kolmar, H., et al., "Alternative binding proteins get mature: Rivalling antibodies", FEBS Journal, vol. 275, 2008, p. 2667.
Krehenbrink, et al. Artificial Binding Proteins (Affitins) as Probes for Conformational Changes in Secretin PulD. J. Mol. Biol. 383 (5): 1058-68 (Abstract) (2008).
McDermott, et al. PD-1 as a potential target in cancer therapy. Cancer Med. 2(5): 662-673 (2013).
Mkrtichyan, et al. Anti-PD1 Antibody Significantly Increases Therapeutic Efficacy of Listeria monocytogenes (Lm)-LLO Immunotherapy. J. Immunotherapy of Cancer, 1:15 (2013.
Merck & Co., Inc., "KEYTRUDA Product Information", U.S. License No. 0002, Revised Oct. 2016, pp. 1-26.

(56) References Cited

OTHER PUBLICATIONS

Merck & Co., Inc., Estimated Overall Survival Rate of 81 Percent at One Year in Patients with Advanced Melanoma, Business Wire NewsHQ, Nov. 18, 2013, 3 pages.
Mkrtichyan, M., et al., "Anti-PD-1 antibody significantly increases therapeutic efficacy of Listeria monocytogenes (Lm)-LLO immunotherapy", Journal for ImmunoTherapy of Cancer, vol. 1 No. 15, Aug. 29, 2013, 7 pages.
National Cancer Institute, "Nivolumab", NCI Drug Dictionary, Dec. 30, 2013, 1 page.
Nishimura, H., et al., "Development of Lupus-like Autoimmune Diseases by Disruption of the PD-1 Gene Encoding an ITIM Motif-Carrying Immunoreceptor", Immunity, vol. 11, Aug. 1999, pp. 141-151.
Nishimura, H., et al., "Developmentally regulated expression of the PD-1 protein on the surface of double negative (CD4~CD8~) thymocytes", International Immunology, vol. 8, No. 5, Feb. 6, 1996, pp. 773-780.
Nishimura, H., et al., "Immunological studies on PD-1-deficient mice: implication of PD-1 as a negative regulator for 3 cell responses", International Immunology, vol. 10, No. 10, Jul. 7, 1998, pp. 1563-1572.
Nygren et al. Alternative binding proteins: affibody binding proteins developed from a small three-helix bundle scaffold. FEBS J. 275 (11): 2668-76 (2008).
Palmer, B.E., et al., "In vivo blockade of the PD-1 receptor suppresses HIV-1 viral loads and improves CD4+ T cell evels in humanized mice." J Immunol., 190(1), Jan. 1, 2013, pp. 211-219.
PCT/IB2015/055943, "International Preliminary Report on Patentability dated Feb. 7, 2017", 13 pages.
PCT/IB2015/055943, "International Search Report and Written Opinion dated Jan. 27, 2016", 26 pages.
Perreau, M., et al., "Follicular helper T cells serve as the major CD4 T cell compartment for HIV-1 infection, replication, and production", The Journal of Experimental Medicine, vol. 210 No. 1, Dec. 17, 2012, pp. 143-156.
Porichis, F., et al., "Role of PD-1 in HIV Pathogenesis and as Target for Therapy", Curr HIV/AIDS Rep. Author Manuscript, Aug. 3, 2012, pp. 1-14.
Seung, E., et al., "PD-1 Blockade in Chronically HIV-1-Infected Humanized Mice Suppresses Viral Loads", PLoS ONE, 8(10): e77780, Oct. 2013, pp. 1-10.
Sievers, et al. Antibody-Drug Conjugates in Cancer Therapy. Ann. Rev. Med. 64: 15-29 (Abstract) (2013).
Siewe, B., et al., "Regulatory B Cells Inhibit Cytotoxic T Lymphocyte (CTL) Activity and Elimination of Infected CD4 T Cells after In Vitro Reactivation of HIV Latent Reservoirs", PLoS ONE, 9(4): e92934, Apr. 16, 2014, pp. 1-9.
Silverman, et al. Corrigendum: Multivalent avimer proteins evolved by exon shuffling of a family of human receptor domains. Nat. Biotechnol. 23 (12): 1556-61 (Abstract) (2005).
Stumpp, et al. DARPins: A new generation of protein therapeutics. Drug Discov. Today 13 (15-16): 695-701 (2008).
Tesaro. Immuno-Oncology Collaboration and License Agreement for TIM-3, LAG-3 and PD-1 Antibody Program. Mar. 13, 2014.
Topalian et al. Safety, Activity, and Immune Correlates of Anti-PD-1 Antibody in Cancer. N. Eng. J. Med. 2012; 366 (26): 2443-2454.
Trautman, et al. Corrigendum: Upregulation of PD-1 expression on HIV-specific CD8+ T cells leads to reversible immune dysfunction. Nat. Med. 12: 1198-1202 (Abstract) (2006).
USAN Council, "Statement on a NonProprietary Name Adopted by The USAN Council USAN (ZZ-165) Lambrolizumab", Jan. 30, 2013, 1 page.
Velu, V., et al., "Enhancing SIV-Specific Immunity In Vivo by PD-1 Blockade", Nature Author Manuscript, Sep. 28, 2009, pp. 1-14.
Weber, J., "Immune checkpoint proteins: a new therapeutic paradigm for cancer-preclinical background: CTLA-4 and PD-1 blockade." (Abstract), Semin Oncol., 37(5), Oct. 2010, 2 pages.
Wikipedia Foundation, Inc., "Programmed cell death 1", Wikipedia, Oct. 8, 2013, 7 pages.
Thou, et al. PD1-based DNA vaccine amplifies HIV-1 GAG-specific CD8+ T cells in mice. J. Clin. Invest. 123(6):2629-2642 (2013).
Zolot, et al. Antibody-drug Conjugates. Nature Rev. Drug. Disc. 12: 259-260 (Abstract) (2013).
Zuberek, K., et al., "The role of in vivo PD-1/PD-LI interactions in syngeneic and allogeneic antitumor responses in murine tumor models.", Blood, vol. 98, No. 11 Part 2, Nov. 16, 2001, 2 pages.

\* cited by examiner

FIG. 1A

Mouse PD-1 (GenBank Accession No. CAA48113.1;

Ishida, et al. EMBO J. 11(11): 3887-3895 (1992))

```
1    mwvrqvpwsf twavlqlswq sgwllevpng pwrsltfypa wltvsegana tftcslsnws
61   edlmlnwnrl spsnqtekqa afcnglsqpv qdarfqiiql pnrhdfhmni ldtrrndsgi
121  ylcgaislhp kakieespga elvvterile tstrypspsp kpegrfqgmv igimsalvgi
181  pvllllawal avfcstsmse argagskddt lkeepsaapv psvayeeldf qgrektpelp
241  tacvhteyat ivfteglgas amgrrgsadg lqgprpprhe dghcswpl
(SEQ ID NO.:140)
```

FIG. 1B

Human PD-1 (GenBank Accession No. AAC51773.1;

Finger, et al. Gene 197(1-2): 177-187 (1997))

```
1    mqipqapwpv vwavlqlgwr pgwfldspdr pwnpptffpa llvvtegdna tftcsfsnts
61   esfvlnwyrm spsnqtdkla afpedrsqpg qdcrfrvtql pngrdfhmsv vrarrndsgt
121  ylcgaislap kaqikeslra elrvterrae vptahspsp  rpagqfqtlv vgvvggllgs
181  lvllvwvlav icsraargti garrtgqplk edpsavpvfs vdygeldfqw rektpeppvp
241  cvpeqteyat ivfpsgmgts sparrgsadg prsaqplrpe dghcswpl
(SEQ ID NO.:141)
```

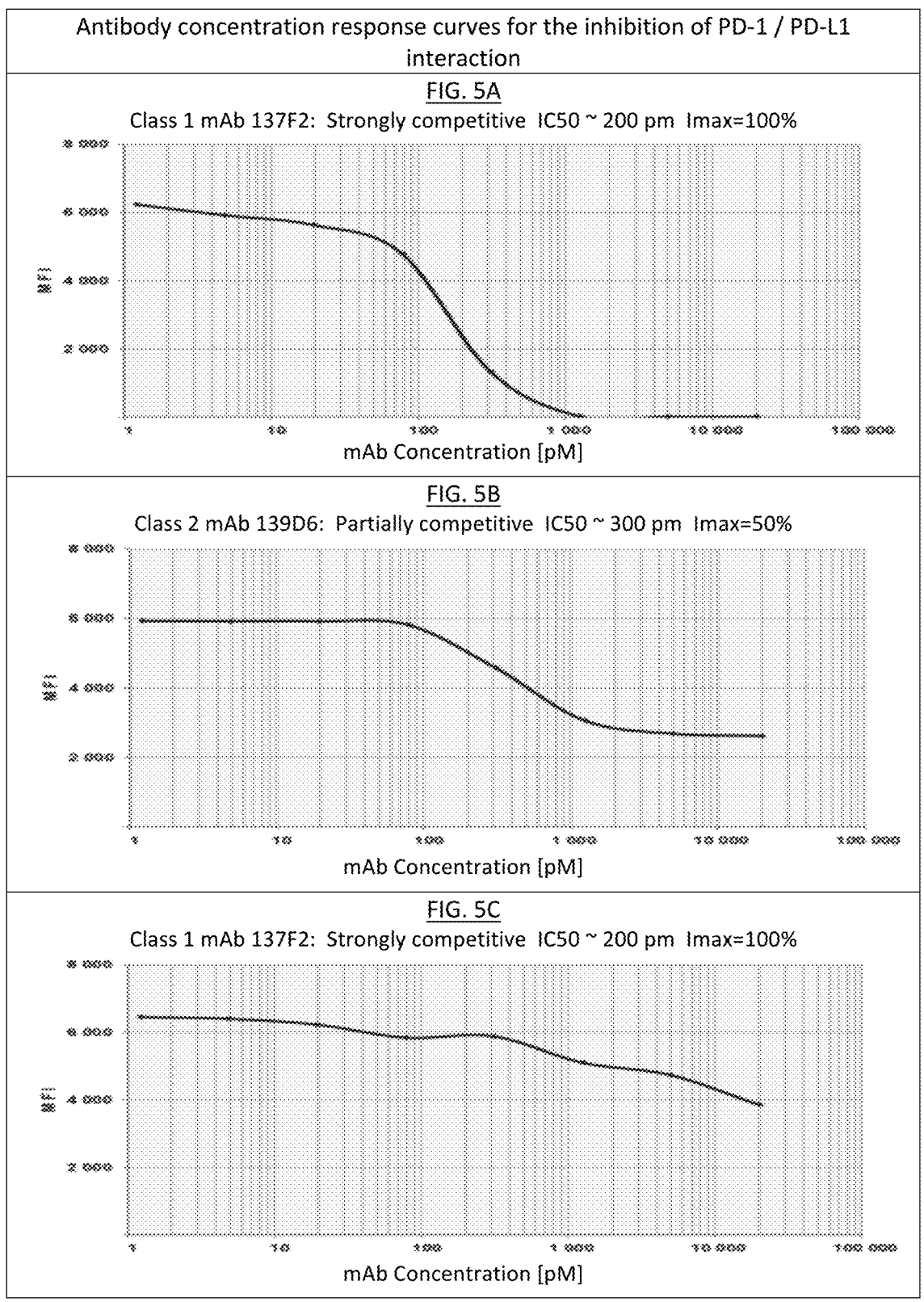

Concentration response curves for Binding of human PD-L1 to human PD-1 Fc

Class 1 mAb 137F2: Strongly competitive

Concentration human PD-L1 [pM]

Class 2 mAb 132F7: Partially competitive

Class 2 mAb 136B4: Non-competitive

— Control without mAb

— Competitor mAb at 20 000 pM

IMMUNOLOGICAL REAGENTS

RELATED APPLICATIONS

This application is a continuation application of U.S. Ser. No. 15/329,760 filed Jan. 27, 2017, now U.S. Pat. No. 9,982,053 B2, which was filed under 35 U.S.C. § 371 and claims priority to International Application No. PCT/IB2015/055943 filed Aug. 5, 2015, and claims priority to U.S. Ser. No. 62/033,177 filed Aug. 5, 2014; U.S. Ser. No. 62/053,366 filed Sep. 22, 2014; and U.S. Ser. No. 62/093,368 filed Dec. 17, 2014; each of which is hereby incorporated by reference into this disclosure in their entirety.

FIELD OF THE DISCLOSURE

This disclosure relates to binding agents with specificity for programmed cell death 1 (PD-1) (e.g., human PD-1) and to methods for using the same to treat and/or prevent infection (e.g., by human immunodeficiency virus (HIV)), cancer and/or autoimmunity.

BACKGROUND OF THE DISCLOSURE

As we enter the fourth decade of the HIV epidemic, significant advances have been made in the understanding of HIV pathogenesis and in the development of potent and safe antiviral drugs. More than 30 antiviral drugs have been registered and the impact of combination antiretroviral therapy (ART) on both morbidity and mortality has been remarkable. However, despite the long-term suppression of HIV replication achieved in patients with optimal adherence to ART, HIV invariably rebounds after interruption of therapy. Furthermore, successful therapy does not induce or allow restoration/development of virus-specific immune responses capable of controlling HIV replication in the absence of ART. Thus, life-long ART is needed to control HIV replication and associated disease in the large majority of HIV infected subjects.

A population of long-lived central memory CD4 T-cells latently infected with HIV has been identified in the blood as an important component of the HIV cell reservoir and as the primary cause of HIV persistence. The life-span of this latent cell reservoir is estimated to be approximately 70 years in the presence of full HIV suppression with ART. However, recent studies have demonstrated that two populations of CD4 T-cells resident in lymph nodes serve as the primary CD4 T-cell compartment for HIV infection, replication and production. These two CD4 T-cell populations are defined by the expression of PD-1 and CXCR5 and include the PD-1+CXCR5+, i.e. T follicular helper cells (Tfh) and PD-1+CXCR5-CD4 T-cell populations.

A number of mechanisms responsible for the establishment and maintenance of the HIV latent cell reservoir(s) have been proposed. One of the mechanisms is the persistent of minimal virus replication under ART which may replenish the HIV cell reservoir. Therefore, ART is unable to induce full suppression of HIV replication and the "natural" HIV-1 specific immune response under ART is also unable to totally suppress and eliminate ongoing residual virus replication. The failures of ART and of the HIV-specific immune response provide the rationale for investigating alternative interventions to target also the persistent HIV cell reservoir.

A number of immunological interventions have been investigated in the past and currently being further developed with the goal to achieve HIV functional cure, wherein viral replication is suppressed without sustained antiviral therapy (9). Therapeutic vaccine strategies have been the primary intervention strategy investigated but the results have shown modest efficacy in experimental animal models and patients with the exception of a CMV-based vector HIV vaccine (50% efficacy in the NHP model;10). Recent studies have generated interesting results on the possibility of using anti-envelope broad neutralizing antibodies (bNabs) as therapeutic agents in HIV infection (11,12). Furthermore, antagonist PD-1 Abs have been shown to restore T-cell functions in HIV infected patients and the possibility to use these Abs as a therapeutic strategy to augment the potency of HIV-specific T-cell responses has been proposed (13,14).

It is well established that infiltrating tumor-specific CD8 T-cells are dysfunctional with regard to their ability to proliferate and to mediate cytotoxic activity. The large majority of infiltrating tumor-specific CD8 T-cells are in a so-called exhaustion functional state. The primary mechanism responsible for the exhaustion of infiltrating tumor-specific CD8 T-cells is the increased expression of a number of regulatory receptors and particularly PD-1 regulatory receptor. The observation that the blockade of the PD-1/PDL-½ (PD-1 ligands) is associated with the recovery of CD8 T-cells from exhaustion has provided the rationale for developing intervention strategies targeting the PD-1 molecule expressed by exhausted_CD8 T-cells. Recent studies have shown very promising results with the use of PD-1 antibodies with antagonist activity in patients with advanced cancer-associated disease. Studies have shown substantial rates of response, ranging from 18 to 40%, in patients with advanced melanoma, non-small cell lung carcinoma and renal carcinoma. Anti-PD-1 antibodies in these studies have been used either alone or in combination with an anti-CTL-A4 antibody. After these initial studies, the current studies are being performed in patients with a variety of tumors including also hematological tumors.

There is a need in the art for additional reagents for targeting PD-1 and methods for using the same. This disclosure addresses those needs by providing reagents and methods that may be used to target PD-1 and cells and/or tissues expressing the same.

BRIEF DESCRIPTION OF THE DRAWINGS

FIG. 1. FIG. 1A. Mouse PD-1. FIG. 1B. Human PD-1.

FIG. 5. Proliferation relative to controls (NEG and Peptide 8). FIG. 5A. Class 1 mAb 137F2: strongly competitive (IC50~200 pM; Imax=100%). FIG. 5B. Class 2 mAb 139D6: partially competitive (IC50~300 pM; Imax=50%). FIG. 5C. Class 2 mAb 136B4: non-competitive.

FIG. 6. Restoration of HIV peptide specific CD8 T-cell proliferation mediated by anti-PD-1 antibodies binding to different epitopes in a functional exhaustion recovery assay.

SUMMARY OF THE DISCLOSURE

Figure 2:
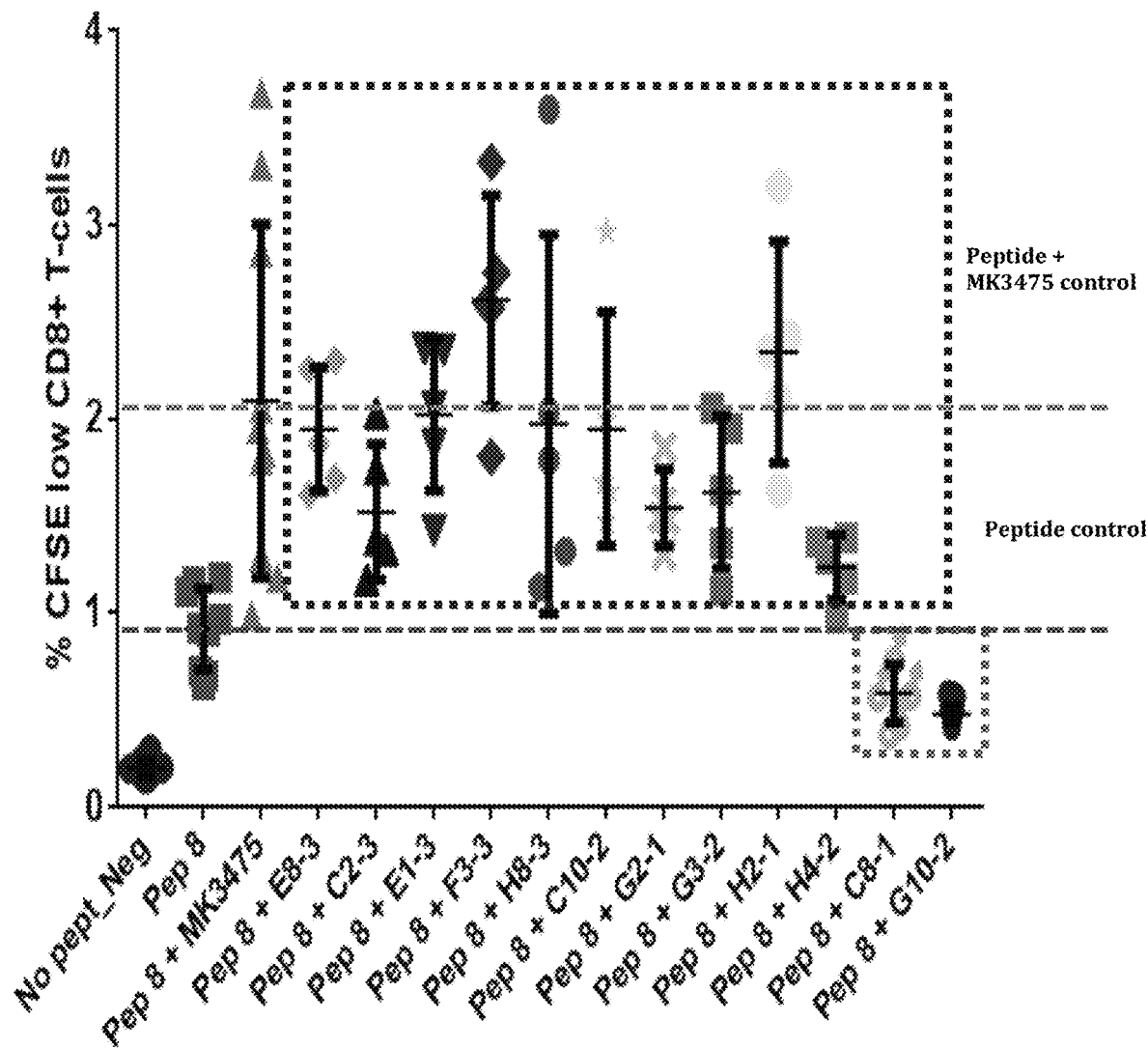
FIG. 2. CFSE assay to evaluate the functional effect of anti-PD1 antibodies on the proliferation of HIV specific CD8 T cells.

This disclosure relates to binding agents with specificity for programmed cell death 1 (PD-1) (e.g., human PD-1) and to methods for using the same such as to treat, prevent and/or ameliorate infection (e.g., by human immunodeficiency virus (HIV)), cancer and/or an autoimmune condition. Functional assays for identifying binding agents that interact with PD-1 are also provided. Combinations of binding agents, such as a first binding agent that blocks the interaction of PD-1 and PD-L1 with a second binding agent that does not block the interaction of PD-1 and PD-L1, are also provided that act synergistically to rescue T cells from exhaustion.

DETAILED DESCRIPTION

This disclosure relates to binding agents that bind programmed cell death (PD-1) protein (e.g., SEQ ID NO:1, FIG. 1A, FIG. 1B of U.S. Pat. No. 5,698,520 (Honjo, et al.) which is hereby incorporated by reference in its entirety) (e.g., human PD-1) on the surface of cells in vitro and/or in vivo. The binding agents may also bind isolated PD-1 polypeptide (e.g., human PD-1) and/or fragments and/or derivatives thereof, typically in vitro. Also provided are methods for using such binding agents to diagnose, treat, prevent and/or ameliorate one or more diseases associated with the existence of cells expressing PD-1. For instance, the binding agents may be antibodies (e.g., monoclonal antibodies) that may react with and/or bind to the epitopes of PD-1. The "binding agents" described herein may include, for example, an agonist or an antagonist of PD-1. An agonist binding agent is one that is not typically capable of restoring T-cell function and/or expression of PD-1. An agonist PD-1 binding agent may be useful for treating autoimmune diseases and others in which PD-1 expressing cells are involved in disease progression. In contrast, an antagonist binding agent is one capable for restoring T-cell function and/or expression of PD-1. For instance, a PD-1 antagonist binding agent may be capable of restoring the function of PD-1 expressing T-cells from functional exhaustion as is known to occur in HIV infection and in a variety of tumors. Restoration of T cell function may be determined by, for instance, measuring proliferation, cytokine production, cytotoxic activity or other characteristics of such cells. Another use for the binding agents described herein is the selective targeting and elimination of HIV-infected CD4 T-cell populations containing replication competent HIV (e.g., in a latent and/or replication state). Such PD-1 expressing cells expressing PD-1 are known to serve as a major cell reservoir for replication competent HIV. A potential mechanism for the elimination of these CD4 T-cell populations is antibody-dependent cellular cytotoxicity (ADCC) using the binding agents described herein (e.g., mono- and/or bi-specific PD-1 antibodies). In some embodiments, one or more PD-1 antagonistic binding agents having, for instance, different specificities (e.g., recognizing different epitopes) may be combined to induce rescue of antigen-specific CD8 T-cells from functional exhaustion caused by PD-1 expression in those cells (e.g., restoring or improving proliferation, cytokine production and/or cytotoxic activity). In some embodiments, the binding agents described herein may also provide for the selective elimination and/or suppression of PD-1 expressing cells. In some embodiments, the PD-1 agonist binding agents described herein may be used to supress and/or eliminate PD-1 expressing cells to treat, for instance, infectious diseases (e.g., HIV), cancer, and/or, especially, autoimmune conditions. Other embodiments, uses and the like are described below.

The binding agents may be antibodies such as monoclonal antibodies that may comprise, for instance, any one or more of the amino acid sequences shown in Table 1 (and/or one or more fragments and/or derivatives thereof). This disclosure also provides for the use of such monoclonal antibodies to isolate, identify, and/or target cells expressing PD-1. In certain embodiments, these monoclonal antibodies may be reactive against PD-1 expressed on the surface of cells. The term "antibody" or "antibodies" may refer to whole or fragmented antibodies in unpurified or partially purified form (e.g., hybridoma supernatant, ascites, polyclonal antisera) or in purified form. The antibodies may be of any suitable origin or form including, for example, murine (e.g., produced by murine hybridoma cells), or expressed as humanized antibodies, chimeric antibodies, human antibodies, and the like. For instance, antibodies may be wholly or partially dervied from human (e.g., IgG (IgG1, IgG2, IgG2a, Ig2b, IgG3, IgG4), IgM, IgA (IgA1 and IgA2), IgD, and IgE), canine (e.g., IgGA, IgGB, IgGC, IgGD), chicken (e.g., IgA, IgD, IgE, IgG, IgM, IgY), goat (e.g., IgG), mouse (e.g., IgG, IgD, IgE, IgG, IgM), and/or pig (e.g., IgG, IgD, IgE, IgG, IgM), rat (e.g., IgG, IgD, IgE, IgG, IgM) antibodies, for instance. Methods of preparing, utilizing and storing various types of antibodies are well-known to those of skill in the art and would be suitable in practicing the present invention (see, for example, Harlow, et al. *Antibodies: A Laboratory Manual*, Cold Spring Harbor Laboratory, 1988; Harlow, et al. *Using Antibodies: A Laboratory Manual, Portable Protocol No. 1*, 1998; Kohler and Milstein, Nature, 256:495 (1975)); Jones et al. Nature, 321:522-525 (1986); Riechmann et al. Nature, 332:323-329 (1988); Presta (Curr. Op. Struct. Biol., 2:593-596 (1992); Verhoeyen et al. (Science, 239:1534-1536 (1988); Hoogenboom et al., J. Mol. Biol., 227:381 (1991); Marks et al., J. Mol. Biol., 222:581 (1991); Cole et al., Monoclonal Antibodies and Cancer Therapy, Alan R. Liss, p. 77 (1985); Boerner et al., J. Immunol., 147(1):86-95 (1991); Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995); as well as U.S. Pat. Nos. 4,816,567; 5,545,807; 5,545,806; 5,569,825; 5,625,126; 5,633,425; and, 5,661,016). In certain applications, the antibodies may be contained within hybridoma supernatant or ascites and utilized either directly as such or following concentration using standard techniques. In other applications, the antibodies may be further purified using, for example, salt fractionation and ion exchange chromatography, or affinity chromatography using Protein A, Protein G, Protein A/G, and/or Protein L ligands covalently coupled to a solid support such as agarose beads, or combinations of these techniques. The antibodies may be stored in any suitable format, including as a frozen preparation (e.g., −20° C. or −70° C.), in lyophilized form, or under normal refrigeration conditions (e.g., 4° C.). When stored in liquid form, for instance, it is preferred that a suitable buffer such as Tris-buffered saline (TBS) or phosphate buffered saline (PBS) is utilized. In some embodiments, the binding agent may be prepared as an injectable preparation, such as in suspension in a non-toxic parenterally acceptable diluent or solvent. Suitable vehicles and solvents that may be utilized include water, Ringer's solution, and isotonic sodium chloride solution, TBS and/or PBS, among others. Such preparations may be suitable for use in vitro or in vivo may be prepared as is known in the art and the exact preparation may depend on the particular application.

However, the binding agents described are not in any way limited to antibodies. For example, the binding agent may be any compound exhibiting similar binding properties as another (e.g., a mimetic). For example, an exemplary binding agent may be one that binds PD-1 and/or can compete with binding agent having specificity therefor (e.g., a monoclonal antibody). In some embodiments, the mimetic may exhibit substantially the same affinity in binding assays as the binding agent (e.g., monoclonal antibody) to which it is being compared. The affinity a particular binding agent may be measured by any suitable assay including but not limited to FACS staining of endogenous cell surface PD-1 on activated CD4 T cells as described in the Examples. One binding agent may be said to have "substantially the same affinity" as another where the measurements (e.g., nm) are within about any of 1-20,1-5,5-10,10-15, or 15-20 percent of one another. Exemplary mimetics may include, for example, organic compounds that specifically bind PD-1, or an affibody (Nygren, et al. FEBS J. 275 (11): 2668-76 (2008)), affilin (Ebersbach, et al. J. Mol. Biol. 372 (1): 172-85 (2007)), affitin (Krehenbrink, et al. J. Mol. Biol. 383 (5): 1058-68 (2008)), anticalin (Skerra, A. FEBS J. 275 (11): 2677-83 (2008)), avimer (Silverman, et al. Nat. Biotechnol. 23 (12): 1556-61 (2005)), DARPin (Stumpp, et al. Drug Discov. Today 13 (15-16): 695-701 (2008)), Fynomer (Grabulovski, et al. J. Biol. Chem. 282 (5): 3196-3204 (2007)), Kunitz domain peptide (Nixon, et al. Curr. Opin. Drug Discov. Devel. 9 (2): 261-8 (2006)), and/or a monobody (Koide, et al. Methods Mol. Biol. 352: 95-109 (2007)). Other mimetics may include, for example, a derivative of an antibody (of, for example, the monoclonal antibody 1E4, 1G10, and/or 1G1) such as, for example, an $F_{ab}$, $F_{ab2}$, Fab' single chain antibody, $F_v$, single domain antibody, monospecific antibody, bi-specific antibody, tri-specific antibody, multi-valent antibody, chimeric antibody, canine-human chimeric antibody, canine-mouse chimeric antibody, antibody comprising a canine Fc, humanized antibody, human antibody, caninized, CDR-grafted antibody, shark antibody, nanobody, canelid antibody, microbody, and/or intrabody, or derivative thereof. Other binding agents are also provided herein as would be understood by one of ordinary skill in the art.

Any method known to those of ordinary skill in the art may be used to generate binding agents having specificity for (e.g., binding to) PD-1. For instance, to generate and isolate monoclonal antibodies an animal such as a mouse may be administered (e.g., immunized) with one or more PD-1 proteins (e.g., PD-1 Fc fusion protein and/or PD-1 His tag protein). Animals exhibiting serum reactivity to PD-1 expressed on activated human T lymphocytes (as determined by, for instance, flow cytometry and/or microscopy) may then be selected for generation of anti-PD-1 hybridoma cell lines. This may be repeated for multiple rounds. For instance, the primary criteria for the first round of binding agent selection may be include but are not limited to: i) level of staining of PD-1 on activated human T lymphocytes by flow cytometry; (ii) diversity of CDR VH and VL sequences as compared to those of the existing anti-PD-1 antibodies; and, (iii) epitope mapping performed by competitive binding studies with PD-1 conjugated Luminex beads pre-coupled with PD-L1 or one of several commercially available anti-PD-1 antibodies binding to different epitopes on PD-1. An exemplary first or second round of selection may also include, for instance, affinity binding (not a primary criteria since it may not correlate with the stimulatory potential of anti-PD-1 antibodies); and/or, functional characterization to identify the binding agent as an agonist or an antagonist.

As described in Example 1 herein, for instance, the Exhaustion Functional Recovery Assay (EFRA) may be used. In this assay, test binding agents may be assayed for the ability to rescue immune cells such as T cells from exhaustion. This may be determined by measuring the ability of a binding agent to restore proliferation to such cells in the presence of an antigen, such as a test peptide derived from a virus such as human immunodeficiency virus (HIV). Proliferation is measured in a CFSE assay in comparison to a control, such as the test peptide alone or a positive control anti-PD-1 antibody such as MK-3475 (pembrolizumab). In some embodiments, a binding agent is determined to restore proliferation where the comparison shows a significant difference (such as a P value of <0.001) compared to either a peptide alone control or peptide with an isotype control mouse IgG1 antibody. This assay may be used to identify binding agents (such as antibodies) that compete with other binding agents for binding to PD-1 (such as PD-L1 or PD-L2) and/or lead to the functional restoration of immune cells. Example 1 also describes two methods of epitope mapping the antibodies listed in Table 2 using Luminex-based assays. In one biochemical assay, a PD-1 Fc fusion protein is bound to beads and competitive binding studies are performed between the anti-PD-1 antibodies described in Table 2 and one of two different commercially available anti-PD-1 antibodies. Example 1 describes four classes of monoclonal antibodies binding to distinct epitopes on PD-1 that were: class 1 (competitive with a first monoclonal antibody that blocks the interaction of PD-1 with PD-L1), class 2 (competitive with a second monoclonal antibody that binds PD-1 but does not block the interaction of PD-1 with PD-L1), class 3 (competitive with both the first and second monoclonal antibodies), and class 4 (non-competitive with either the first or second antibodies). In a separate assay, competition for binding to a recombinant PD-1 protein was evaluated for the anti-PD-1 antibodies listed in Table 2 and a biotinylated PD-L1 recombinant protein. Antibodies that induced proliferation in the EFRA were identified from all four binding classes that are proposed of binding to different epitopes on PD-1. Likewise, the EFRA allowed for the identification of anti-PD-1 antibodies that were either competitive, partially competitive or non-competitive with the PD-1/PD-L1 interaction and specifically restored proliferative function to HIV specific CD8 T-cell.

Combinations of binding agents may also be identified, such as those described in Example 2. In some embodiments, the combinations may be identified to provide statistically significant differences from results obtained using only one or more of the binding agents and not others. In some embodiments, combinations exhibiting synergistic ability to restore immune cell function may be identified. In some embodiments, the combination may comprise a first binding agent that blocks the interaction of PD-1 and PD-L1 with a second binding agent that does not block the interaction of PD-1 and PD-L1. The first and second binding agents may be different entities such as two or more different monoclonal antibodies or derivatives thereof, or may be found on the same entity such as a bi-functional antibody (a single antibody or derivative thereof comprising multiple binding specificities). For instance, an exemplary bi-functional antibody may comprise a first binding region that blocks the interaction of PD-1 and PD-L1 and a second binding region that does not block the interaction of PD-1 and PD-L1. Also contemplated are combinations that provide multiple types of each binding agent. For instance, the combination may comprise multiple types of binding agents that block the interaction of PD-1 and PD-L1 with one or more that does not block the interaction of PD-1 and PD-L1. In some embodiments, the combination may comprise one or more of binding agents that block the interaction of PD-1 and PD-L1 with multiple binding agents that do not block the interaction of PD-1 and PD-L1. In some embodiments, the combination may comprise multiple binding agents that block the interaction of PD-1 and PD-L1 with multiple binding agents that do not block the interaction of PD-1 and PD-L1. Such combinations as described herein may also be combined with one or more other agents that may effect immune cell function such as antibodies against CTLA-4 and the like. One of ordinary skill in the art would recognize that many such combinations may be suitable for use as described herein.

Where the binding agent is an antibody, it may be identified with reference to the nucleotide and/or amino acid sequence corresponding to the variability and/or complementarity determining regions ("CDRs") thereof. The variable region/CDR sequences may be used in combination with one or more other variable region/CDR amino acid sequences. The variable region/CDR amino acid sequences may alternatively and/or also be adjoined to one or more types of constant region polypeptides of an antibody molecule. For instance, the CDR amino acid sequences shown in Tables 1A and 1B may be adjoined to or associated with the constant regions of any antibody molecule of the same or a different species (e.g., human, goat, rat, sheep, chicken) and/or antibody subtype of that from which the CDR amino acid sequence was derived. For instance, an exemplary binding agent may be, or may be derived from, or may be related to the monoclonal antibody produced by the hybridomas listed in, and/or may have about the same affinity and/or proliferation effect, and/or exhibit the same binding class shown in Table 2, and/or may have any one or more of the amino acid sequences of SEQ ID NOS. 1-138 and/or as shown in Tables 1A and 1B. The binding agent may comprise an antibody heavy and/or a light chain that each comprises one or more constant and/or variable regions. The variable regions typically comprise one or more CDRs that may determine the binding specificity of the antibody. The monoclonal antibodies may also be identified by analysis of the amino acid sequences of (e.g., which may be encoded by such nucleotide sequences) such variable regions. For instance, exemplary amino acid sequences of the heavy chain CDRs of binding agents that bind PD-1 may include any one or more of comprising at least one amino acid sequence selected from the group consisting of SEQ ID NOS. 1-138, and/or any other shown in Tables 1A and/or 1B. Any of the amino acid sequences described herein, and/or any fragments and/or derivatives thereof may also be combined with any other variable region and/or CDR in any order and/or combination to form hybrid and/or fusion binding agents and/or inserted into other heavy and/or light chain variable regions using standard techniques. Exemplary combinations of CDRs (e.g., combination of heavy and/or light chain CDR1, CDR2 and CDR3 amino acid sequences) that may be found in a PD-1 (e.g., human PD-1) binding agent of this disclosure may include, for instance, the embodiments shown in Tables 1A and/or 1B.

TABLE 1A

Heavy chain: Amino acids sequence

| Clone | CDR1 | CDR2 | CDR3 |
|---|---|---|---|
| 122F10 | DDFLH (SEQ ID NO: 1) | RIDPANGESRYAPKFQD (SEQ ID NO: 24) | TDYRGYYYAMDY (SEQ ID NO: 47) |
| 139D6 | NYYIH (SEQ ID NO: 2) | SIYPNYGDTNYNQKVKD (SEQ ID NO: 25) | GYSYAMDY (SEQ ID NO: 48) |
| 135D1 | NYYIH (SEQ ID NO: 3) | SIYPNYGETNYNQEFKG (SEQ ID NO: 26) | GYSYAMDY (SEQ ID NO: 49) |
| 134D2 | SNWMH (SEQ ID NO: 4) | AVNPGNSDTTYNQKFKG (SEQ ID NO: 27) | GRSYDGSFDY (SEQ ID NO: 50) |
| 121G1 | RYWMH (SEQ ID NO: 5) | NIDPSDSTTHYNPKFRD (SEQ ID NO: 28) | DLDDFYVGSHEDFDY (SEQ ID NO: 51) |
| 136B5 | SNWMH (SEQ ID NO: 6) | AVYPGNSDTTYNQNFKG (SEQ ID NO: 29) | GRSYDGSFDY (SEQ ID NO: 52) |
| 127C2 | NSYIH (SEQ ID NO: 7) | WISPGDGSTNYNEKFKG (SEQ ID NO: 30) | EEYDYDNY (SEQ ID NO: 53) |
| 137F2 | NYWIG (SEQ ID NO: 8) | DIYPGGGYTNYNEKFKG (SEQ ID NO: 31) | GYDFVLDR (SEQ ID NO: 54) |
| 138H5 | SYAMS (SEQ ID NO: 9) | TISGGGADTYYLDNVKG (SEQ ID NO: 32) | QRGENLFAH (SEQ ID NO: 55) |
| 140A1 | SDYAWN (SEQ ID NO: 10) | YINYSGYTNYNPFLKS (SEQ ID NO: 33) | YGGSYPWNFDV (SEQ ID NO: 56) |
| 135H12 | SYWIN (SEQ ID NO: 11) | NIYPGSSSIDYNEKFKS (SEQ ID NO: 34) | GLYWYFDV (SEQ ID NO: 57) |

TABLE 1A-continued

Heavy chain: Amino acids sequence

| Clone | CDR1 | CDR2 | CDR3 |
|---|---|---|---|
| 131D11 | SSYIH (SEQ ID NO: 12) | WIFPGDGKTNYNEKFRD (SEQ ID NO: 35) | NDFDRGVY (SEQ ID NO: 58) |
| 132F7 | NHGMS (SEQ ID NO: 13) | SINTGGYSTYYPDNVKG (SEQ ID NO: 36) | DDYNWFAY (SEQ ID NO: 59) |
| 126E4 | NYWIG (SEQ ID NO: 14) | DIYPGSEYENYNEKFKG (SEQ ID NO: 37) | GYDFVLDH (SEQ ID NO: 60) |
| 135G1 | DSYIH (SEQ ID NO: 15) | RIDPAHGNVIYASKFRD (SEQ ID NO: 38) | IYYDYGEGDF (SEQ ID NO: 61) |
| 136E10 | DTYIH (SEQ ID NO: 16) | RIDLANDDILYASKFQG (SEQ ID NO: 39) | IYYDYGEGDY (SEQ ID NO: 62) |
| 135C12 | NFYIH (SEQ ID NO: 17) | SIYPNYGDTAYNQKFKD (SEQ ID NO: 40) | GYSYAMDY (SEQ ID NO: 63) |
| 136F4 | DSYIH (SEQ ID NO: 18) | RIDPARDNIIYASKFRD (SEQ ID NO: 41) | IYYDYGEGDY (SEQ ID NO: 64) |
| 136B4 | DDFLH (SEQ ID NO: 19) | RIDPANGESRYAPQFQD (SEQ ID NO: 42) | TDYRGYYYAMDY (SEQ ID NO: 65) |
| 135E10 | SYFMS (SEQ ID NO: 20) | GISTGGADTYYADSMKG (SEQ ID NO: 43) | LSHYYDGIPLDC (SEQ ID NO: 66) |
| 140G5 | NHGMS (SEQ ID NO: 21) | SISGGGDNTYYPDNLKG (SEQ ID NO: 44) | VRQLGLHRAAMDY (SEQ ID NO: 67) |
| 122H2 | NYWIG (SEQ ID NO: 22) | DIYPGGDHKNYNEKFKD (SEQ ID NO: 45) | GFDFVLDY (SEQ ID NO: 68) |
| 139F11 | SFAMS (SEQ ID NO: 23) | TITGGGVNTYYPDTVKG (SEQ ID NO: 46) | QAIYDGHYVLDY (SEQ ID NO: 69) |

TABLE 1B

Light chain: Amino acids sequence

| Clone | CDR1 | CDR2 | CDR3 |
|---|---|---|---|
| 122F10 | KSSQSVLYSSNQKNYLA (SEQ ID NO: 70) | WASTRES (SEQ ID NO: 93) | HQYLSSYT (SEQ ID NO: 116) |
| 139D6 | SASQGISDGLN (SEQ ID NO: 71) | HTSTLHS (SEQ ID NO: 94) | QQYSKFPLT (SEQ ID NO: 117) |
| 135D1 | SASQGISNGLN (SEQ ID NO: 72) | HTSTLHS (SEQ ID NO: 95) | QQYSKFPLT (SEQ ID NO: 118) |
| 134D2 | KASQDINKYIA (SEQ ID NO: 73) | YTSTLRP (SEQ ID NO: 96) | LQYDNLWT (SEQ ID NO: 119) |
| 121G1 | RSSQSIVYSNGNTYLE (SEQ ID NO: 74) | KVSHRFS (SEQ ID NO: 97) | FQGSHVPYT (SEQ ID NO: 120) |
| 136B5 | KASQDINKYMA (SEQ ID NO: 75) | YTSTLRP (SEQ ID NO: 98) | LQYDNLWT (SEQ ID NO: 121) |
| 127C2 | KASQNVGTNVG (SEQ ID NO: 76) | SASYRYN (SEQ ID NO: 99) | QQYNTYPWT (SEQ ID NO: 122) |
| 137F2 | KSSQSLFNSETQKNYLA (SEQ ID NO: 77) | WASTRES (SEQ ID NO: 100) | KQSYTLRT (SEQ ID NO: 123) |
| 138H5 | LASQTIGTWLA (SEQ ID NO: 78) | AATSLAD (SEQ ID NO: 101) | QQLYSTPWT (SEQ ID NO: 124) |
| 140A1 | RSSQTIVHNNGDTYLE (SEQ ID NO: 79) | KISNRFF (SEQ ID NO: 102) | FQGSHVPYT (SEQ ID NO: 125) |

TABLE 1B-continued

Light chain: Amino acids sequence

| Clone | CDR1 | CDR2 | CDR3 |
|---|---|---|---|
| 135H12 | KSSQSLFNSGTRKNYLA (SEQ ID NO: 80) | WASTRDS (SEQ ID NO: 103) | KQSYNLYT (SEQ ID NO: 126) |
| 131D11 | KASQNVDTNVA (SEQ ID NO: 81) | SASYRYN (SEQ ID NO: 104) | QQYNNYPYT (SEQ ID NO: 127) |
| 132F7 | KSSQSLLNSGNQKNYLT (SEQ ID NO: 82) | WASTRES (SEQ ID NO: 105) | QSDYSYPLT (SEQ ID NO: 128) |
| 126E4 | KSSQSLFNSGTRKSYLA (SEQ ID NO: 83) | WASTRET (SEQ ID NO: 106) | MQSYNLRT (SEQ ID NO: 129) |
| 135G1 | HASQNINVWLS (SEQ ID NO: 84) | KASNLHT (SEQ ID NO: 107) | QQGQSWPLT (SEQ ID NO: 130) |
| 136E10 | HASQNINVWLS (SEQ ID NO: 85) | KASNLHT (SEQ ID NO: 108) | QQGQSYPLT (SEQ ID NO: 131) |
| 135C12 | SASQGISGDLN (SEQ ID NO: 86) | HTSSLHS (SEQ ID NO: 109) | QYYSKDLLT (SEQ ID NO: 132) |
| 136F4 | HASQNINVWLS (SEQ ID NO: 87) | KASNLHT (SEQ ID NO: 110) | QQGQSWPLT (SEQ ID NO: 133) |
| 136B4 | KSSQSVLYSSNQKNYLA (SEQ ID NO: 88) | WASTRES (SEQ ID NO: 111) | HQYLSSYT (SEQ ID NO: 134) |
| 135E10 | RASESVDNSGVSFLT (SEQ ID NO: 89) | AASNQGS (SEQ ID NO: 112) | QQTKEVPWT (SEQ ID NO: 135) |
| 140G5 | KASQSVSDDVS (SEQ ID NO: 90) | SAFFRYP (SEQ ID NO: 113) | QQDYSSPLT (SEQ ID NO: 136) |
| 122H2 | KSSQSLFNSGTRKNYLA (SEQ ID NO: 91) | WASTRES (SEQ ID NO: 114) | MQSFNLRT (SEQ ID NO: 137) |
| 139F11 | RTSGNIHNYLA (SEQ ID NO: 92) | NVKTLTD (SEQ ID NO: 115) | QQFWSIPWT (SEQ ID NO: 138) |

In addition, any of SEQ ID NOS. 1-69 may be combined with any one or more of SEQ ID NOS. 70-138 into a binding agent. In preferred embodiments, the heavy chain CDRs of each clone are combined with their respective light chain CDRs into a binding agent. In some embodiments, the binding agent may comprise the heavy chain CDRs and light chain CDRs shown below:

122F10 (SEQ ID NOS. 1, 24, 47, 70, 93, and 116);
139D6 (SEQ ID NOS. 2, 25, 48, 71, 94, and 117);
135D1 (SEQ ID NOS. 3, 26, 49, 72, 95, and 118);
134D2 (SEQ ID NOS. 4, 27, 50, 73, 96, and 119);
121G1 (SEQ ID NOS. 5, 28, 51, 74, 97, and 120);
136B5 (SEQ ID NOS. 6, 29, 52, 75, 98, and 121);
127C2 (SEQ ID NOS. 7, 30, 53, 76, 99, and 122);
137F2 (SEQ ID NOS. 8, 31, 54, 77, 100, and 123);
138H5 (SEQ ID NOS. 9, 32, 55, 78, 101, and 124);
140A1 (SEQ ID NOS. 10, 33, 56, 79, 102, and 125);
135H12 (SEQ ID NOS. 11, 34, 57, 80, 103, and 126);
131D11 (SEQ ID NOS. 12, 35, 58, 81, 104, and 127);
132F7 (SEQ ID NOS. 13, 36, 59, 82, 105, and 128);
126E4 (SEQ ID NOS. 14, 37, 60, 83, 106, and 129);
135G1 (SEQ ID NOS. 15, 38, 61, 84, 107, and 130);
136E10 (SEQ ID NOS. 16, 39, 62, 85, 108, and 131);
135C12 (SEQ ID NOS. 17, 40, 63, 86, 109, and 132);
136F4 (SEQ ID NOS. 18, 41, 64, 87, 110, and 133);
136B4 (SEQ ID NOS. 19, 42, 65, 88, 111, and 134);
135E10 (SEQ ID NOS. 20, 43, 66, 89, 112, and 135);
140G5 (SEQ ID NOS. 21, 44, 67, 90, 113, and 136);
122H2 (SEQ ID NOS. 22, 45, 68, 91, 114, and 137); or
139F11 (SEQ ID NOS. 23, 46, 69, 92, 115, and 138).

Other combinations may also be useful as may ascertained by one of ordinary skill in the art.

Binding agents comprising the CDRs of Tables 1A and/or 1B, or those of the immediately preceding paragraph, may also exhibit the following characteristics:

TABLE 2

| Clone | Affinity* (nM) | Binding Class** | Antibody competition with the PD-1/PD-L1 interaction*** | EFRA % relative to peptide stimulation alone‡ |
|---|---|---|---|---|
| 122F10 | 2.2 | 4 | Non-competitive | 146% |
| 139D6 | 2.4 | 2 | Partial competition | 195% |
| 135D1 | 6.5 | 2 | Partial competition | 187% |
| 134D2 | 4.8 | 4 | Competitive | 205% |
| 121G1 | 11.9 | 4 | Non-competitive | 120% |
| 136B5 | 7.7 | 4 | Competitive | 200% |
| 127C2 | 1.0 | 2 | Non-competitive | 100% |
| 137F2 | 1.5 | 1 | Competitive | 250% |
| 138H5 | 1.6 | 3 | Competitive | 210% |
| 140A1 | 1.4 | 3 | Competitive | 160% |
| 135H12 | 1.9 | 1 | Competitive | 190% |
| 131D11 | 2.7 | 1 | Competitive | 180% |
| 132F7 | 100 | 2 | Non-competitive | 210% |
| 126E4 | 0.5 | 4 | Competitive | 130% |
| 135G1 | 32 | 4 | NA | 138% |
| 136E10 | 7.1 | 4 | Non-competitive | 148% |
| 135C12 | 1.7 | 2 | Partial competition | 195% |
| 136F4 | 8.3 | 4 | Non-competitive | 108% |

TABLE 2-continued

| Clone | Affinity* (nM) | Binding Class** | Antibody competition with the PD-1/PD-L1 interaction*** | EFRA % relative to peptide stimulation alone‡ |
|---|---|---|---|---|
| 136B4 | 1.4 | 2 | Non-competitive | 185% |
| 135E10 | 1.5 | 3 | Competitive | 165% |
| 140G5 | 1.6 | 1 | Competitive | 205% |
| 122H2 | 4.3 | 1 | Competitive | 200% |
| 139F11 | 3.1 | 1 | Competitive | 250% |

*Binding affinity for the antibodies listed in Table 1 was evaluated by FACS staining of endogenous cell surface PD-1 on activated CD4 T cells.
**Binding class was determined by Luminex assay competitive binding studies. Binding class 1 mAb clones are competitive with the EH12.2H7 clone commercial antibody, class 2 mAb clones are competitive with the J116 clone commercial antibody, class 3 mAb clones are competitive with both EH12.2H7 and J116 antibodies and class 4 mAb clones bind in the presence of both EH12.2H7 and J116 antibodies.
***Antibody competition with the PD-1/PD-L1 interaction was determined in a second Luminex binding assay. In this assays, PD-1 Fc fusion protein coated beads were incubated in the absence or presence of an anti-PD-1 antibody from Table 2 at a concentration of 20 nM. A fixed concentration of 1.25 nM biotinylated PD-L1, approximately equivalent to the $IC_{50}$ of the PD-1/PD-L1 interaction, was then incubated with the PD-1/antibody complex and PD-L1 binding was detected by fluorescence with phycoerythrin labeled streptavidin. Based on PD-L1 binding to the PD-1/antibody complex, antibodies were defined as being competitive, partially competitive or non-competitive with the PD-1/PD-L1 interaction.
‡Proliferative effect is evaluated using a CFSE assay (an embodiment of the Exhaustion Functional Recovery Assay, "EFRA"). PBMCs isolated from a chronically infected HIV subject were stimulated with an HIV specific peptide in the presence and absence of an anti-PD-1 antibody. Following a 6 day incubation, proliferation of HIV specific CD8 T cells was evaluated in the anti-PD-1 treated samples relative to the peptide alone control.
NA = not available Binding affinity may be determined by any technique available to those of ordinary skill in the art. The binding affinity data presented in Table 2 was evaluated by flow cytometry staining of endogenous cell surface PD-1 on CD4 T cells that were stimulated for a period of 3 to 6 days with phytohaemagglutinin (PHA). Binding class may also be determined by any technique available to those of ordinary skill in the art. The binding class data presented in Table 2 was determined by Luminex assay competitive binding studies. In Table 2, binding class 1 mAb antibodies are those determined to be competitive with the EH12.2H7 clone commercial antibody (available from BioLegend, San Diego, Calif.(e.g., Cat. No. 329905)); class 2 antibodies are those determined to be competitive with the J116 clone commercial antibody (available from Affymetrix eBioscience, San Diego, Calif. (e.g., Cat. No. 16-9989-80)); and class 3 antibodies are those determined to be competitive with both EH12.2H7 and J116 antibodies; and class 4 mAb clone antibodies are those determined to bind PD-1 in the presence of both EH12.2H7 and J116 antibodies.

Proliferative effect may be determined by any technique available to those of ordinary skill in the art. For instance, the EFRA system described above and used in Example 1 may be used. Such an assay was used to determine the proliferative effect data presented in Table 2. Briefly, a carboxyfluorescein succinimidyl ester (CFSE) assay in which peripheral blood mononuclear cells (PBMCs) were isolated from a chronically infected HIV subject and stimulated with an HIV-specific peptide in the presence and absence of an anti-PD-1 antibody. A control anti-PD1 antibody (the Merck antibody MK-3475) was also tested as a positive control. Following a six-day incubation, proliferation of HIV-specific CD8 T cells was evaluated in the anti-PD-1 treated samples relative to the peptide alone control and the result expressed as a percentage above control ("Proliferation effect").

In some embodiments, the techniques used to identify and characterize PD-1 binding agents such as antibodies may be combined to provide a system for identifying and characterizing such binding agents. For instance, one or more candidate binding agents such one or more monoclonal antibodies may be assayed by EFRA or a similar assay to determine the ability of the candidate binding agent to restore function to immune cells as measured by, for instance, proliferation in the presence of an immunogenic peptide. In some embodiments, this type of assay may be used as an initial screen to ensure the candidate binding agents to be further studied are capable of restoring immune cell function. In some embodiments, these types of assays may be followed by one for determining the binding affinity to immune cells such as activated peripheral blood mononuclear cells (PBMCs). In some embodiments, this assay may use a technique such as fluorescence activated cell sorting (FACS). In some embodiments, the assay may include the presence or absence of non-specific binding and/or competitive binding studies using known binding reagents such as anti-PD1 antibody (e.g., the Merck antibody MK-3475, also known as pembrolizumab). These assays may then be followed by sequencing of the CDRs of the candidate binding agents such as provided in Tables 1A and/or 1B above. Together, then, the EFRA, affinity determination, epitope mapping studies and CDR identification methods described herein provide a system with which a candidate binding agent may be identified.

Any of the amino acid sequences of Tables 1A and/or 1B (and/or any one or more fragments and/or derivatives thereof) may be also substituted by any other amino acid as desired by one of ordinary skill in the art. For example, one of skill in the art may make conservative substitutions by replacing particular amino acids with others as shown in Table 3 below. The specific amino acid substitution selected may depend on the location of the site selected. Such conservative amino acid substitutions may involve a substitution of a native amino acid residue with a non-native residue such that there is little or no effect on the size, polarity, charge, hydrophobicity, or hydrophilicity of the amino acid residue at that position and, in particular, does not result in decreased PD-1 binding.

TABLE 3

| Original Amino Acid Residues in SEQ ID NOS. 1-138 | Exemplary Conservative Substitutions of the Original Amino Acid Residues of SEQ ID NOS. 1-138 | Preferred ConservativeSubstitution of the Original Amino Acid Residues of SEQ ID NOS. 1-138 |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

In some embodiments, this disclosure provides binding agents with multiple specificities such that PD-1 and at least one other secondary antigen (e.g., a cell surface protein) may be bound by a single binding agent. In some embodiments, the secondary antigen may be one expressed by cells infected by an infectious agent. For instance, an exemplary secondary antigen may be HIV Env antigen. Such binding agents may bind the secondary antigen and/or may serve to neutralize the infectious agent. In certain embodiments, such as for a bi-specific binding agent having dual specificity for PD-1 and an HIV antigen such as env and/or another antigen, for instance. The HIV immunogen may be derived from any of the subtypes described herein, or any other. In some embodiments, such binding agents may include: PD-1 agonist/Env binding; PD-1 agonist PD-1/Env binding and neutralization; PD-1 antagonist/Env binding; and/or PD-1 antagonist/PD-1/Env binding and neutralization. Given the prevalence of the various subtypes, it may be preferable to select antigens from HIV-1 subtypes B and/or C. It may also be desirable to include binding agents having specificity for antigens from multiple HIV subtypes (e.g., HIV-1 subtypes B and C, HIV-2 subtypes A and B, or a combination of HIV-1 and HIV-2 subtypes) in a single composition. For treating a disease such as cancer, it may be beneficial to obtain binding agents with multiple PD-1 specificities (e.g., bi-specific PD-1a/PD1b antagonist PD-1 antibodies specific to two different epitopes) and/or specificity to both PD-1 and one or more tumor antigens (e.g., cancer-testis (CT) antigen (i.e., MAGE, NY-ESO-1); melanocyte differentiation antigen (i.e., Melan A/MART-1, tyrosinase, gp100); mutational antigen (i.e., MUM-1, p53, CDK-4); overexpressed 'self' antigen (i.e., HER-2/neu, p53); and/or viral antigens (i.e., HPV, EBV)). The binding agents (e.g., monoclonal antibodies) may be generated as generally described above. The specificities of such binding agents may be recombined into a single binding agent using techniques that are widely available to those of ordinary skill in the art. In some embodiments, multiple single specificity binding agents may also be combined and used (e.g., administered) to provide an effective multiple specificity reagent.

In some embodiments, the binding agents described herein may be conjugated to active agents to target and inhibit the function of and /or eliminate cell populations expressing PD-1 (and/or another antigen in the case of binding agents with multiple specificities). For instance, $CD4^+$ T-cell populations containing replication competent HIV may be targeted and eliminated using binding agent/drug conjugates (e.g., antibody-drug conjugates (ADC)). Mono- and/or bi-specific candidate binding agents may be conjugated with one or more types of drugs (e.g., drugs damaging DNA, targeting microtubules). The binding agents described herein and/or derivatives thereof may also be adjoined to and/or conjugated to functional agents for in vitro and/or in vivo use. For instance, the binding agent may be adjoined to and/or conjugated to functional moieties such as cytotoxic drugs or toxins, and/or active fragments thereof such as diphtheria A chain, exotoxin A chain, ricin A chain, abrin A chain, curcin, crotin, phenomycin, enomycin, among others. Suitable functional moieties may also include radiochemicals. Binding agents, such as antibodies, may be adjoined to and/or conjugated to the one or more functional agents using standard techniques in the art.

In some embodiments, the binding agents may be administered in conjunction with other agents such as anti-infective agents (e.g., antibiotics, anti-viral medications). For instance, the binding agents described herein may be combined with monoclonal antibodies and/or other reagents such as Nivolumab (also known as MDX-1106, BMS-936558 (Topalian, et al. N. Eng. J. Med. 2012; 366(26): 2443-2454), MDX-1106, ONO-4538, a fully human IgG4 mAb available from Bristol-Myers Squibb), Lambrolizumab (also known as MK-3475 and SCH 900475, a humanized IgG4 monoclonal antibody available from Merck), Pidilizumab (a humanized IgG1 monoclonal antibody available from CureTech), AMP-224 (a B7-DC/IgG1 fusion protein available from GlaxoSmithKline/Amplimmune), and/or an antibody or other reagent or method described in any of U.S. Pat. No. 8,354,509B2 (Carven, et al), U.S. Pat. No. 8,008,449B2 (Korman, et al), WO 2012/135408A1 (Manoj, et al.), US 2010/026617 (Carven, et al.), WO 2011/110621A1 (Tyson, et al), U.S. Pat. No. 7,488,802B2 (Collins, et al.), WO 2010/029435A1 (Simon, et al.), WO 2010/089411A2 (Olive, D.), WO 2012/145493A1 (Langermann, et al.), WO 2013/0435569A1 (Rolland, et al.), WO 2011/159877A2 (Kuchroo, et al.), U.S. Pat. No. 7,563,869B2 (Ono Pharm.), U.S. Pat. No. 7,858,746B2 (Honjo, et al.), U.S. Pat. No. 8,728,474B2 (Ono Pharm.), U.S. Pat. No. 9,067,999 (Ono Pharm.), and/or U.S. Pat. No. 9,067,999, each of which is hereby incorporated in its entirety into this disclosure.

As mentioned above, the PD-1 binding agents described herein (e.g., a PD-1 antagonist) may be used to treat and/or prevent and/or ameliorate the symptoms of infection by HIV. As is well-known in the art, HIV isolates are now classified into discrete genetic subtypes. HIV-1 is known to comprise at least ten subtypes (A1, A2, A3, A4, B, C, D, E, F1, F2, G, H, J and K) (Taylor et al, NEJM, 359(18):1965-1966 (2008)). HIV-2 is known to include at least five subtypes (A, B, C, D, and E). Subtype B has been associated with the HIV epidemic in homosexual men and intravenous drug users worldwide. Most HIV-1 immunogens, laboratory adapted isolates, reagents and mapped epitopes belong to subtype B. In sub-Saharan Africa, India and China, areas where the incidence of new HIV infections is high, HIV-1 subtype B accounts for only a small minority of infections, and subtype HIV-1 C appears to be the most common infecting subtype. Any of these types of isolates may be addressed using the binding agents described herein. One or more binding agents may also be administered with or in conjunction with one or more agents used to prevent, treat and/or ameliorate HIV such as for example, a protease inhibitor, an HIV entry inhibitor, a reverse transcriptase inhibitor, and/or an anti-retroviral nucleoside analog. Suitable compounds include, for example, Agenerase (amprenavir), Combivir (Retrovir/Epivir), Crixivan (indinavir), Emtriva (emtricitabine), Epivir (3tc/lamivudine), Epzicom, Fortovase/Invirase (saquinavir), Fuzeon (enfuvirtide), Hivid (ddc/zalcitabine), Kaletra (lopinavir), Lexiva (Fosamprenavir), Norvir (ritonavir), Rescriptor (delavirdine), Retrovir/AZT (zidovudine), Reyatax (atazanavir, BMS-232632), Sustiva (efavirenz), Trizivir (abacavir/zidovudine/lamivudine), Truvada (Emtricitabine/Tenofovir DF), Videx (ddI/didanosine), Videx EC (ddI, didanosine), Viracept (nevirapine), Viread (tenofovir disoproxil fumarate), Zerit (d4T/stavudine), and Ziagen (abacavir) may be utilized. Other suitable agents are known to those of skill in the art and may be suitable for use as described herein. Such agents may either be used prior to, during, or after administration of the binding agents and/or use of the methods described herein.

As mentioned above, the PD-1 binding agents described herein (e.g., a PD-1 antagonist) may be used to treat and/or prevent and/or ameliorate the symptoms of cancer. Exemplary cancers may include, for instance, any of the breast, blood, colon, stomach, rectum, skeletal tissue, skin (e.g., melanoma) brain, lung, bladder, kidney, ovary, and/or liver, among others. One or more of the binding agents may also be combined with and/or administered with or in conjunction with one or more agents used to prevent, treat and/or ameliorate cancer such as for example, an alkylating agent (e.g., any nitrogen mustard, nitrosourea, tetrazine, aziridine, cisplatin and/or derivative thereof), anti-metabolite (e.g., any of the methotrexates, pemetrexeds, fluoropyrimidines and/or derivative thereof), anti-microbtubule agent (e.g., vinca alkyloids, taxanes, podophyllotoxin and/or derivative thereof), topoisomerase I and/or II inhibitors (e.g., a camptothecin, irinotecan, topotecan, etoposide, doxorubicin, mitoxantrone, teniposide, novobiocin, merbarone, aclarubicin and/or derivative thereof) and/or cytotoxic antibiotic (e.g., any anthracyclines, actinomycin, bleomycin, plicamycin, and mitomycin and/or derivative thereof). The one or more binding agents may also, or alternatively, be combined with one or more other binding agents available to those of ordinary skill in the art for treating, preventing and/or ameliorating cancer such as, for example, Nivolumab, Lambrolizumab, Pidilizumab and/or other similar agents and/or derivatives thereof. Other suitable agents are known to those of skill in the art and may be suitable for use as described herein. Such agents may either be used prior to, during, or after administration of the binding agents and/or use of the methods described herein.

As mentioned above, the PD-1 binding agents described herein (e.g., a PD-1 agonist) may be used to treat and/or prevent and/or ameliorate the symptoms of autoimmunity. Exemplary autoimmune conditions may include, for instance, any in which PD-1 is involved in maintaining self-tolerance and/or one involving inflammatory T cells (e.g., autoreactive or self antigen-specific T cells) such as, for instance, systemic lupus erythematosus (SLE), type I diabetes, rheumatoid arthritis, glomerulonephritis, and multiple sclerosis. Such PD-1 binding agents may also be combined with other agents such as anti-CTLA-4 agents (e.g., ipilimumab). One or more of the binding agents may also be combined with and/or administered with or in conjunction with one or more agents used to prevent, treat and/or ameliorate autoimmunity such as, for example, glucocorticoids, cytostatics (e.g., alkylating agent, anti-metabolite, methotrexate, azathioprine, mercaptopurine, cytotoxic antibiotics (e.g., dactinomycin, anthracyclines, mitomycin C, bleomycin, mithramycin), antibodies (e.g., Atgam, Thymoglobuline, Simulect, Zenapax), drugs acting on immunophilins (e.g., ciclosporin, tacrolimus, sirolimus), interferons, opioids, TNF-binding agents (e.g., Remicade, Enbrel, Humira), mycophenolate, fingolimod, myriocin, and/or derivatives thereof. Other suitable agents are known to those of skill in the art and may be suitable for use as described herein. Such agents may either be used prior to, during, or after administration of the binding agents and/or use of the methods described herein.

In some embodiments, the binding agents may be adjoined to and/or conjugated to one or more detectable labels. For instance, suitable detectable labels may include, for instance, fluoresceins (e.g., DyLight, Cy3, Cy5, FITC, HiLyte Fluor 555, HiLyte Fluor 647; 5-carboxy-2,7-dichlorofluorescein; 5-Carboxyfluorescein (5-FAM); 5-HAT (Hydroxy Tryptamine); 5-Hydroxy Tryptamine (HAT); 6-JOE; 6-carboxyfluorescein (6-FAM); FITC; 6-carboxy-1,4-dichloro-2',7'-dichlorofluorescein (TET); 6-carboxy-1,4-dichloro-2', 4', 5', 7'-tetra-chlorofluorescein (HEX); 6-carboxy-4', 5'-dichloro-2', 7'-dimethoxyfluorescein (JOE); Alexa fluors (e.g., 350, 405, 430, 488, 500, 514, 532, 546, 555, 568, 594, 610, 633, 635, 647, 660, 680, 700, 750); BODIPY fluorophores (e.g., 492/515, 493/503, 500/510, 505/515, 530/550, 542/563, 558/568, 564/570, 576/589, 581/591, 630/650-X, 650/665-X, 665/676, FL, FL ATP, Fl-Ceramide, R6G SE, TMR, TMR-X conjugate, TMR-X, SE, TR, TR ATP, TR-X SE)), rhodamines (e.g., 110, 123, B, B 200, BB, BG, B extra, 5-carboxytetramethylrhodamine (5-TAMRA), 5 GLD, 6-Carboxyrhodamine 6G, Lissamine, Lissamine Rhodamine B, Phallicidine, Phalloidine, Red, Rhod-2, ROX (6-carboxy-X-rhodamine), 5-ROX (carboxy-X-rhodamine), Sulphorhodamine B can C, Sulphorhodamine G Extra, TAMRA (6-carboxytetramethyl-rhodamine), Tetramethylrhodamine (TRITC), WT), Texas Red, and/or Texas Red-X. Other detectable labels known in the art may also be suitable for use. Binding agents, such as antibodies, may be adjoined to and/or conjugated to the one or more detectable labels using standard techniques in the art.

In certain embodiments, a nucleic acid molecule encoding one or more binding agents described herein may be inserted into one or more expression vectors, as discussed below in greater detail. In such embodiments, the binding agent may be encoded by nucleotides corresponding to the amino acid sequence. The particular combinations of nucleotides (codons) that encode the various amino acids (AA) are well known in the art, as described in various references used by those skilled in the art (e.g., Lewin, B. Genes V, Oxford University Press, 1994). The nucleotide sequences encoding the amino acids of said binding agents may be ascertained with reference to Table 4, for example. Nucleic acid variants may use any combination of nucleotides that encode the binding agent.

TABLE 4

Codons Encoding Amino Acids (AA) of SEQ ID NOS. 1-138 of Variants Thereof

| AA | Codon | AA | Codons | AA | Codons | AA | Codons |
|---|---|---|---|---|---|---|---|
| Phe (F) | TTT | Ser (S) | TCT | Tyr (Y) | TAT | Cys (C) | TGT |
|  | TTC |  | TCC |  | TAC |  | TGC |
| Leu (L) | TTA |  | TCA | TERM | TAA | TERM | TGA |
|  | TTG |  | TCG |  | TAG | Trp (W) | TGG |
|  | CTT | Pro (P) | CCT | His (H) | CAT | Arg (R) | CGT |
|  | CTC |  | CCC |  | CAC |  | CGC |
|  | CTA |  | CCA | Gln (Q) | CAA |  | CGA |
|  | CTG |  | CCG |  | CAG |  | CGG |
| Ile (I) | ATT | Thr (T) | ACT | Asn (N) | AAT | Ser (S) | AGT |
|  | ATC |  | ACC |  | AAC |  | AGC |
|  | ATA |  | ACA | Lys (K) | AAA | Arg (R) | AGA |
| Met (M) | ATG |  | ACG |  | AAG |  | AGG |
| Val (V) | GTT | Ala (A) | GCT | Asp (D) | GAT | Gly (G) | GGT |
|  | GTC |  | GCC |  | GAC |  | GGC |
|  | GTA |  | GCA | Glu (E) | GAA |  | GGA |
|  | GTG |  | GCG |  | GAG |  | GGG |

Those of ordinary skill in the art understand that the nucleotide sequence encoding a particular amino acid sequence may be easily derived from the amino acid sequence and the information presented in Table 4. For instance, it may be deduced from the amino acid sequence DDFLH (SEQ ID NO.: 1) and the information presented in Table 4 that the amino acid sequence may be encoded by the nucleotide sequence GAT GAT TTT TTA CAT (SEQ ID NO.:139). Those of ordinary skill in the art would understand that nucleotide sequences encoding SEQ ID NOS. 2-138 may be deduced in the same way, and such nucleotide sequences are contemplated herein. Where the binding agents are antibodies, nucleotide sequences encoding the variable regions thereof may also be isolated from the phage and/or hybridoma cells expressing the same cloned into expression vectors to produce certain preparations (e.g., humanized antibodies). Methods for producing such preparations are well-known in the art.

To determine the amino acid sequences of the variable regions (e.g., CDRs) of interest, hybridoma cells from mice immunized with a PD-1 antigen/immunogen may be selected using the functional assays described herein and cloning techniques that are readily available to those of ordinary skill in the art. For instance, to isolate and sequence nucleic acids encoding the heavy and light chain variable regions of the selected hybridomas, total RNA may be extracted from fresh hybridoma cells using TRIzol reagent according to the manufacturer's protocol. cDNA may be synthesized from the RNA using isotype-specific anti-sense primers or universal primers using standard techniques (e.g., following the technical manual of PrimeScript™ 1st Strand cDNA Synthesis Kit). Polymerase chain reaction (PCR) may then be performed to amplify the nucleic acids encoding the variable regions (heavy and light chains) of the antibody produced by the selected hybridoma, which may then be cloned into a standard cloning vector separately and sequenced. Colony PCR screening may then be performed to identify clones with inserts of correct sizes. Preferably, no less than five single colonies with inserts of correct sizes are sequenced for each antibody variable region. Standard protocols may then be used for the expression and purification of the anti-PD-1 antibodies. For instance, hybridoma clones may be grown in serum-free medium and the cell culture broth centrifuged and then filtered. The filtered supernatant containing the antibody may then be loaded onto an affinity column (e.g., Protein A) column, washed and eluted with an appropriate buffer (e.g., Pierce IgG elute buffer). The eluted fractions may then be pooled and buffer-exchanged into PBS, pH 7.2. The purified antibody may then be analyzed by SDS-PAGE and Western blot by using standard protocols for molecular weight, yield and purity. Size exclusion chromatography HPLC may then be performed on an appropriate column (e.g., TSK GEL-G3000 SWXL column (Tosoh)) for biophysical characterization in order to ensure high antibody purity (generally >90%) with low presence of protein aggregates. These procedures were used in isolating and sequencing nucleic acids encoding SEQ ID NOS. 1-138 from selected hybridoma cells. These techniques, variations thereof, and/or other may also be of use for these purposes as would be understood by those of ordinary skill in the art.

Nucleic acid molecules encoding one or more PD-1 binding agents may be contained within a viral and/or a non-viral vector. In one embodiment, a DNA vector is utilized to deliver nucleic acids encoding one or more PD-1 binding agents to the patient. In doing so, various strategies may be utilized to improve the efficiency of such mechanisms including, for example, the use of self-replicating viral replicons (Caley, et al. 1999. *Vaccine,* 17: 3124-2135; Dubensky, et al. 2000. *Mol. Med.* 6: 723-732; Leitner, et al. 2000. *Cancer Res.* 60: 51-55), codon optimization (Liu, et al. 2000. *Mol. Ther.,* 1: 497-500; Dubensky, supra; Huang, et al. 2001. *J. Virol.* 75: 4947-4951), in vivo electroporation (Widera, et al. 2000. *J. Immunol.* 164: 4635-3640), incorporation of nucleic acids encoding co-stimulatory molecules, cytokines and/or chemokines (Xiang, et al. 1995. *Immunity,* 2: 129-135; Kim, et al. 1998. *Eur. J. Immunol.,* 28: 1089-1103; Iwasaki, et al. 1997. *J. Immunol.* 158: 4591-3601; Sheerlinck, et al. 2001. *Vaccine,* 19: 2647-2656), incorporation of stimulatory motifs such as CpG (Gurunathan, supra; Leitner, supra), sequences for targeting of the endocytic or ubiquitin-processing pathways (Thomson, et al. 1998. *J. Virol.* 72: 2246-2252; Velders, et al. 2001. *J. Immunol.* 166: 5366-5373), prime-boost regimens (Gurunathan, supra; Sullivan, et al. 2000. *Nature,* 408: 605-609; Hanke, et al. 1998. *Vaccine,* 16: 439-445; Amara, et al. 2001. *Science,* 292: 69-74), proteasome-sensitive cleavage sites, and the use of mucosal delivery vectors such as *Salmonella* (Darji, et al. 1997. *Cell,* 91: 765-775; Woo, et al. 2001. *Vaccine,* 19: 2945-2954). Other methods are known in the art, some of which are described below. Various viral vectors that have been successfully utilized for introducing a nucleic acid to a host include retrovirus, adenovirus, adeno-associated virus (AAV), herpes virus, and poxvirus, among others. The vectors may be constructed using standard recombinant techniques widely available to one skilled in the art. Such techniques may be found in common molecular biology references such as *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), and *PCR Protocols: A Guide to Methods and Applications* (Innis, et al. 1990. Academic Press, San Diego, Calif.). "Non-viral" plasmid vectors may also be suitable in certain embodiments. Preferred plasmid vectors are compatible with bacterial, insect, and/or mammalian host cells. Such vectors include, for example, PCR-ii, PCR3, and pcDNA3.1 (Invitrogen, San Diego, Calif.), pBSii (Stratagene, La Jolla, Calif.), pet15 (Novagen, Madison, Wis.), pGEX (Pharmacia Biotech, Piscataway, N.J.), pEGFp-n2 (Clontech, Palo Alto, Calif.), pETI (Bluebacii, Invitrogen), pDSR-alpha (PCT pub. No. WO 90/14363) and pFASTBACdual (Gibco-BRL, Grand island, N.Y.) as well as Bluescript® plasmid derivatives (a high copy number COLe1-based phagemid, Stratagene Cloning Systems, La Jolla, Calif.), PCR cloning plasmids designed for cloning TAQ-amplified PCR products (e.g., TOPO™ TA cloning® kit, PCR2.1® plasmid derivatives, Invitrogen, Carlsbad, Calif.). Bacterial vectors may also be used. These vectors include, for example, *Shigella, Salmonella, Vibrio cholerae, Lactobacillus,* Bacille Calmette Guérin (BCG), and *Streptococcus* (see for example, WO 88/6626; WO 90/0594; WO 91/13157; WO 92/1796; and WO 92/21376). Many other non-viral plasmid expression vectors and systems are known in the art and may be use. Other delivery techniques may also suffice including, for example, DNA-ligand complexes, adenovirus-ligand-DNA complexes, direct injection of DNA, $CaPO_4$ precipitation, gene gun techniques, electroporation, and colloidal dispersion systems. Colloidal dispersion systems include macromolecule complexes, nanocapsules, microspheres, beads, and lipid-based systems including oil-in-water emulsions, micelles, mixed micelles, and liposomes. The preferred colloidal system is a liposome, which are artificial membrane vesicles useful as delivery vehicles in vitro and in vivo. RNA, DNA and intact virions can be encapsulated within the aqueous interior and be delivered to cells in a biologically active form (Fraley, R., et al., 1981, *Trends Biochem. Sci.,* 6: 77). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

A cultured cell comprising the vector is also provided. The cultured cell may be a cultured cell transfected with the vector or a progeny of the cell, wherein the cell expresses the immunogenic polypeptide. Suitable cell lines are known to those of skill in the art and are commercially available, for example, through the American Type Culture Collection (ATCC). The transfected cells can be used in a method of producing an immunogenic polypeptide. The method comprises culturing a cell comprising the vector under conditions that allow expression of the immunogenic polypeptide, optionally under the control of an expression sequence. The immunogenic polypeptide can be isolated from the cell or the culture medium using standard protein purification methods.

The skilled artisan has many suitable techniques for using the binding agents (e.g., antibodies) described herein to identify biological samples containing proteins that bind thereto. For instance, antibodies may be utilized to isolate PD-1 using, for example, immunoprecipitation or other capture-type assay. This well-known technique is performed by attaching the antibody to a solid support or chromatographic material (e.g., a bead coated with Protein A, Protein G and/or Protein L). The bound antibody is then introduced into a solution either containing or believed to contain the PD-1 (e.g., an HIV-infected T cell lysate). PD-1 may then bind to the antibody and non-binding materials are washed away under conditions in which the PD-1 remains bound to the antibody. The bound protein may then be separated from the antibody and analyzed as desired. Similar methods for isolating a protein using an antibody are well-known in the art. The binding agents (e.g., antibodies) may also be utilized to detect PD-1 within a biological sample. For instance, the antibodies may be used in assays such as, for example, flow cytometric analysis, ELISA, immunoblotting (e.g., western blot), in situ detection, immunocytochemistry, and/or immunhistochemistry. Methods of carrying out such assays are well-known in the art.

The binding agents described herein may be also be used to determine the presence of a disease state in a patient, to predict prognosis, or to determine the effectiveness of a chemotherapeutic or other treatment regimen. Expression profile assays, performed as described herein or as is otherwise known in the art, may be used to determine the relative level of expression of PD-1. The level of expression may then be correlated with base (e.g., control) levels to determine whether a particular disease is present within the patient, the patient's prognosis, or whether a particular treatment regimen is effective. For example, if the patient is being treated with a particular anti-infective regimen, an increased or decreased level of expression of PD-1 in the patient's tissues (e.g., in peripheral blood, breast tissue biopsy) may indicate the regimen is worsening or improving the load of the infectious agent in that host. The increase or decrease in expression may indicate the regimen is having or not having the desired effect and another therapeutic modality may therefore be selected.

It is also possible to use the binding agents described herein as reagents in drug screening assays to test, for example, new drug candidates. The reagents may be used to ascertain the effect of a drug candidate on the expression of the immunogenic target in a cell line, or a cell or tissue of a patient. The expression profiling technique may be combined with high throughput screening techniques to allow rapid identification of useful compounds and monitor the effectiveness of treatment with a drug candidate (see, for example, Zlokarnik, et al., Science 279, 84-8 (1998)). Drug candidates may be chemical compounds, nucleic acids, proteins, antibodies, or derivatives therefrom, whether naturally occurring or synthetically derived. Drug candidates thus identified may be utilized, among other uses, as pharmaceutical compositions for administration to patients or for use in further screening assays.

In some embodiments, the binding agents are in purified form. A "purified" binding agent (e.g., antibody) may be one that is separated from at least about 50% of the proteins and/or other components with which it is initially found (e.g., as part of a hybridoma supernatant or ascites preparation in the case of a monoclonal antibody). A purified binding agent (e.g., antibody) may be one that is separated from at least about 50%, 60%, 75%, 90%, or 95% of the proteins and/or other components with which it is initially found.

The polypeptides and nucleic acids described herein may be combined with one or more pharmaceutically acceptable carriers prior to administration to a host. A pharmaceutically acceptable carrier is a material that is not biologically or otherwise undesirable, e.g., the material may be administered to a subject, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. Suitable pharmaceutical carriers and their formulations are described in, for example, *Remington's: The Science and Practice of Pharmacy*, $21^{st}$ Edition, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally from about 5 to about 8 or from about 7 to about 7.5. Other carriers include sustained-release preparations such as semipermeable matrices of solid hydrophobic polymers containing polypeptides or fragments thereof. Matrices may be in the form of shaped articles, e.g., films, liposomes or microparticles. It will be apparent to those persons skilled in the art that certain carriers may be more preferable depending upon, for instance, the route of administration and concentration of composition being administered. Carriers are those suitable for administration of polypeptides and/or fragments thereof to humans or other subjects. Pharmaceutical compositions may also include carriers, thickeners, diluents, buffers, preservatives, surface active agents, adjuvants, immunostimulants, in addition to the immunogenic polypeptide. Pharmaceutical compositions may also include one or more active ingredients such as antimicrobial agents, antiinflammatory agents and anesthetics. The pharmaceutical composition may be administered orally, parentally, by inhalation spray, rectally, intranodally, or topically in dosage unit formulations containing conventional pharmaceutically acceptable carriers, adjuvants, and vehicles. The term "pharmaceutically acceptable carrier" or "physiologically acceptable carrier" as used herein refers to one or more formulation materials suitable for accomplishing or enhancing the delivery of a nucleic acid, polypeptide, or peptide as a pharmaceutical composition. A "pharmaceutical composition" is a composition comprising a therapeutically effective amount of a nucleic acid or polypeptide. The terms "effective amount" and "therapeutically effective amount" each refer to the amount of a binding agent, nucleic acid or the like used to observe the desired therapeutic effect (e.g., restore T cell function).

Methods for treating one or more disease conditions (e.g., HIV or cancer) in a mammalian host comprising administering to the mammal at least one or more effective doses of one or more binding agents (and/or derivative(s) thereof) described herein are also provided. In some embodiments, the binding agent is a monoclonal antibody or fragment or derivative thereof comprising one or more of SEQ ID NOS. 1-138 and/or shown in Tables 1A and 1B. The one or more binding agents may be administered in a dosage amount of about 1 to about 50 mg/kg, about 1 to about 30 mg/kg, or about 5 to about 30 mg/kg (e.g., about any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, or 40 mg/kg). In certain embodiments, the one or more binding agents may be administered to the mammal (e.g., intradermally, intravenously, orally, rectally) at about 10 mg/kg one or more times. When multiple doses are administered, the doses may comprise about the same or different amount of binding agent in each dose. The doses may also be separated in time from one another by the same or different intervals. For instance, the doses may be separated by about any of 6, 12, 24, 36, 48, 60, 72, 84, or 96 hours, one week, two weeks, three weeks, one month, two months, three months, four months, five months, six months, seven months, eight months, nine months, 10 months, 11 months, 12 months, 1.5 years, 2 years, 3 years, 4 years, 5 years, or any time period before, after, and/or between any of these time periods. In some embodiments, the binding agents may be administered in conjunction with other agents (e.g., anti-infective agents and/or chemotherapeutic agent). Such other agents may be administered about simultaneously with the binding agents, or at a different time and/or frequency. Other embodiments of such methods may also be appropriate as could be readily determined by one of ordinary skill in the art.

To assist the skilled artisan in using the antibodies described herein, the same may be provided in kit format. A kit including such antibodies and optionally other components necessary for using the antibodies to detect cells expressing PD-1 is provided. The antibodies of the kit may be provided in any suitable form, including frozen, lyophilized, or in a pharmaceutically acceptable buffer such as TBS or PBS. The kit may also include other reagents required for utilization of the antibodies in vitro or in vivo such as buffers (e.g., TBS, PBS), blocking agents (solutions including nonfat dry milk, normal sera, Tween-20 Detergent, BSA, or casein), and/or detection reagents (e.g., goat anti-mouse IgG biotin, streptavidin-HRP conjugates, allophycocyanin, B-phycoerythrin, R-phycoerythrin, peroxidase, detectable labels, and other labels and/or staining kits (e.g., ABC Staining Kit, Pierce)). The kits may also include other reagents and/or instructions for using the antibodies in commonly utilized assays described above such as, for example, flow cytometric analysis, ELISA, immunoblotting (e.g., western blot), in situ detection, immunocytochemistry, immunhistochemistry. In one embodiment, the kit provides a binding agent in purified form. In another embodiment, the binding agent may be provided in biotinylated form either alone or along with an avidin-conjugated detection reagent (e.g., antibody). In another embodiment, the kit includes a binding agents comprising one or more detectable labels that may be used to directly detect PD-1. Buffers and the like required for using any of these systems are well-known in the art and/or may be prepared by the end-user or provided as a component of the kit. The kit may also include a solid support containing positive- and negative-control protein and/or tissue samples. For example, kits for performing spotting or western blot-type assays may include control cell or tissue lysates for use in SDS-PAGE or nylon or other membranes containing pre-fixed control samples with additional space for experimental samples. Kits for visualization of PD-1 in cells on slides may include pre-formatted slides containing control cell or tissue samples with additional space for experimental samples. Other embodiments of kits are also contemplated herein as would be understood by those of ordinary skill in the art.

Thus, this disclosure provides a binding agent that binds PD-1 agonistically or antagonistically. In some embodiments, the binding agent is a polypeptide comprising at least one amino acid sequence selected from the group consisting of SEQ ID NOS. 1-138 and/or shown in Tables 1A and 1B. In some embodiments, the binding agent is a polypeptide comprising one or more combinations of SEQ ID NOS. 1-138 (e.g., as shown in Tables 1A and/or 1B). In some embodiments, the binding agent is an antibody. In some embodiments, the binding agent is a polypeptide such as an antibody comprising a heavy chain CDR1 amino acid sequence selected from the group consisting of SEQ ID NOS. 1-23. In some embodiments, the binding agent is a polypeptide such as an antibody comprising a heavy chain CDR2 amino acid sequence selected from the group consisting of SEQ ID NOS. 24-46. In some embodiments, the binding agent is a polypeptide such as an antibody comprising a heavy chain CDR3 amino acid sequence selected from the group consisting of 47-69. In some embodiments, the binding agent is a polypeptide such as an antibody comprising a light chain CDR1 amino acid sequence selected from the group consisting of SEQ ID NOS. 70-92. In some embodiments, the binding agent is a polypeptide such as an antibody comprising a heavy chain CDR2 amino acid sequence selected from the group consisting of SEQ ID NOS. 93-115. In some embodiments, the binding agent is a polypeptide such as an antibody comprising a heavy chain CDR3 amino acid sequence selected from the group consisting of 116-138. In some embodiments, the binding agent comprises the combinations of CDRs shown in Tables 1A and/or 1B and/or has the properties described in Table 2. In some embodiments, the binding agent is derived from or related to (e.g., by sequence or derivation) a human antibody, human IgG, human IgG1, human IgG2, human IgG2a, human IgG2b, human IgG3, human IgG4, human IgM, human IgA, human IgA1, human IgA2, human IgD, human IgE, canine antibody, canine IgGA, canine IgGB, canine IgGC, canine IgGD, chicken antibody, chicken IgA, chicken IgD, chicken IgE, chicken IgG, chicken IgM, chicken IgY, goat antibody, goat IgG, mouse antibody, mouse IgG, pig antibody, and/or rat antibody, and/or a derivative thereof. In some embodiments, the derivative may be selected from the group consisting of an $F_{ab}$, $F_{ab2}$, Fab' single chain antibody, $F_v$, single chain, mono-specific antibody, bispecific antibody, trimeric antibody, multi-specific antibody, multivalent antibody, chimeric antibody, canine-human chimeric antibody, canine-mouse chimeric antibody, antibody comprising a canine Fc, humanized antibody, human antibody, caninized antibody, CDR-grafted antibody, shark antibody, nanobody, and/or canelid antibody. In some embodiments, the binding agent comprises at least a first and second specificity, the first being against PD-1 and the second being against a different antigen (e.g., an antigen of an infectious agent such as HIV (e.g., env) and/or a tumor antigen). In some embodiments, the binding agent and/or derivative thereof may comprise a detectable label fixably attached thereto. In some embodiments, the binding agent of any one and/or derivative thereof comprises an effector moiety (e.g., a cytotoxic drug, toxin, diphtheria A chain, exotoxin A chain, ricin A chain, abrin A chain, curcin, crotin, phenomycin, enomycin, and radiochemical) fixably attached thereto. In some embodiments, polynucleotides encoding one or more binding agents are also provided (e.g., as an expression vector). Host cells comprising and/or expressing the polypeptide products of such polynucleotides are also provided. In some embodiments, compositions comprising at least one binding agent or derivative; at least one isolated polynucleotide; at least one expression vector; and/or, at least one host cell; or a combination thereof; and, a pharmaceutically acceptable carrier are also provided.

This disclosure also provides methods for detecting PD-1 on a cell, the method comprising contacting a test biological sample with a binding agent or derivative described herein and detecting the binding agent bound to the biological sample or components thereof. Such methods may be an in vivo method or an in vitro method. In some embodiments, the method may comprise comparing the amount of binding to the test biological sample or components thereof to the amount of binding to a control biological sample or components thereof, wherein increased binding to the test biological sample or components thereof relative to the control biological sample or components thereof indicates the presence of a cell expressing PD-1 in the test biological sample (e.g., mammalian blood). In some embodiments, a system for identifying a PD-1 antibody binding agent by assaying the candidate binding agent by the exhaustion functional recovery assay (EFRA); determining the affinity of the candidate binding agent for PD-1; and, determining the nucleotide sequence of the CDR of the candidate binding agent is provided.

In some embodiments, a kit for detecting the expression of PD-1 in or on a cell, the kit comprising a binding agent or derivative thereof and instructions for use. In some embodiments, the binding agent and/or derivative thereof is in lyophilized form.

In some embodiments, this disclosure provides methods for treating, preventing and/or ameliorating an infectious disease, cancer and/or autoimmunity in a mammal comprising administering to the mammal at least one effective dose of a pharmaceutical composition comprising a binding agent or derivative thereof. In some embodiments, the infectious disease is human immunodeficiency virus (HIV). In some embodiments, the binding agent and/or derivative thereof used to treat infectious disease and/or cancer is a PD-1 antagonist. In some embodiments, the binding agent and/or derivative thereof used to treat an autoimmune condition is a PD-1 agonist. In some embodiments, multiple doses are administered to the animal. In some embodiments, the binding agent and/or derivative thereof may be administered in a dosage amount of about 1 to 50 mg/kg.

This disclosure also provides combinations of PD-1 binding agents. In some embodiments, the combination comprises a first binding agent that blocks the interaction of PD-1 and PD-L1 and a second binding agent that does not block the interaction of PD-1 and PD-L1. Such combinations may be used for any use described herein or as may be otherwise ascertained by those of ordinary skill in the art. For instance, such combinations may be used in the methods for treating, preventing and/or ameliorating an infectious disease, cancer and/or autoimmunity in a mammal described herein.

This disclosure also provides methods for producing the binding agents described herein by expressing the binding agent in a cell and isolating the binding agent from the cell or a culture supernatant of the cell. In some embodiments, such methods may further comprise expressing a nucleic acid encoding such binding agent(s). In some embodiments, such methods may also include combining the binding agent(s) following isolation with one or more pharmaceutically acceptable excipients.

Methods for producing a combination(s) of binding agents, such as a first binding agent that blocks the interaction of PD-1 and PD-L1 and a second binding agent that does not block the interaction of PD-1 and PD-L1, are also provided by this disclosure. In some embodiments, the second binding agent binds PD-1. In some embodiments, the first and/or second binding agents are antibodies such monoclonal antibodies or fragments or derivatives thereof. In some embodiments, the second binding agent comprises the amino acid sequences SEQ ID NOS. 2, 25, 48, 71, 94 and 117; or SEQ ID NOS. 17, 40, 63, 86, 109, and 132. In some embodiments, these methods may further include the addition of a pharmaceutically acceptable excipient.

The terms "about", "approximately", and the like, when preceding a list of numerical values or range, refer to each individual value in the list or range independently as if each individual value in the list or range was immediately preceded by that term. The terms mean that the values to which the same refer are exactly, close to, or similar thereto.

As used herein, a subject or a host is meant to be an individual. The subject can include domesticated animals, such as cats and dogs, livestock (e.g., cattle, horses, pigs, sheep, and goats), laboratory animals (e.g., mice, rabbits, rats, guinea pigs) and birds. In one aspect, the subject is a mammal such as a primate or a human.

Optional or optionally means that the subsequently described event or circumstance can or cannot occur, and that the description includes instances where the event or circumstance occurs and instances where it does not. For example, the phrase optionally the composition can comprise a combination means that the composition may comprise a combination of different molecules or may not include a combination such that the description includes both the combination and the absence of the combination (i.e., individual members of the combination).

Ranges may be expressed herein as from about one particular value, and/or to about another particular value. When such a range is expressed, another aspect includes from the one particular value and/or to the other particular value. Similarly, when values are expressed as approximations, by use of the antecedent about or approximately, it will be understood that the particular value forms another aspect. It will be further understood that the endpoints of each of the ranges are significant both in relation to the other endpoint, and independently of the other endpoint. Ranges (e.g., 90-100%) are meant to include the range per se as well as each independent value within the range as if each value was individually listed.

The term "combined" or "in combination" or "in conjunction" may refer to a physical combination of agents that are administered together or the use of two or more agents in a regimen (e.g., administered separately, physically and/or in time) for treating, preventing and/or ameliorating a particular disease.

When the terms treat, prevent, and/or ameliorate or derivatives thereof are used herein in connection with a given treatment for a given condition (e.g., preventing cancer infection by HIV), it is meant to convey that the treated patient either does not develop a clinically observable level of the condition at all, or develops it more slowly and/or to a lesser degree than he/she would have absent the treatment. These terms are not limited solely to a situation in which the patient experiences no aspect of the condition whatsoever. For example, a treatment will be said to have prevented the condition if it is given during exposure of a patient to a stimulus that would have been expected to produce a given manifestation of the condition, and results in the patient's experiencing fewer and/or milder symptoms of the condition than otherwise expected. For instance, a treatment can "prevent" infection by resulting in the patient's displaying only mild overt symptoms of the infection; it does not imply that there must have been no penetration of any cell by the infecting microorganism.

Similarly, reduce, reducing, and reduction as used herein in connection with prevention, treatment and/or amelioration of a given condition by a particular treatment typically refers to a subject developing an infection more slowly or to a lesser degree as compared to a control or basal level of developing an infection in the absence of a treatment (e.g., administration of one or more PD-1 binding agents). A reduction in the risk of infection may result in the patient's displaying only mild overt symptoms of the infection or delayed symptoms of infection; it does not imply that there must have been no penetration of any cell by the infecting microorganism.

All references cited within this disclosure are hereby incorporated by reference in their entirety. Certain embodiments are further described in the following examples. These embodiments are provided as examples only and are not intended to limit the scope of the claims in any way.

EXAMPLES

Example 1

Generation and Characterization of PD-1 Binding Agents

Four mice strains (total of 16 mice) have been immunized with two PD-1 proteins, i.e. human PD-1 Fc fusion protein and a human PD-1 monomeric protein. Mice showing serum reactivity to PD-1 expressed on activated human T lymphocytes have been selected for generation of anti-PD-1 hybridoma cell lines. A total of 240 PD-1 hybridoma cell lines were selected for producing antibodies that bind to recombinant PD-1 protein. The primary criteria for the first round of antibodies selection were: i) staining of PD-1 on activated human T lymphocytes by flow cytometry; ii) diversity of CDR VH and VL sequences as compared to those of the existing anti-PD-1 antibodies; and, iii) epitope mapping performed by competitive binding studies with PD-1 conjugated Luminex beads with two commercially available anti-PD-1 antibodies binding to different epitopes on PD-1. A second round of selection was then carried out by: iv) affinity binding assays (not a primary criteria as it does not correlate with the stimulatory potential of anti-PD-1 antibodies); v) evaluation of anti-PD-1 antibodies that bind PD-1 and are either competitive, partially competitive or non-competitive with the binding of PD-L1 in a Luminex biochemical assay; and, vi) functional characterization of antibodies as agonist (not able to restore T-cells from functional exhaustion) or antagonist (able to restore T-cells from functional exhaustion). In these studies, the antibodies were tested and differentiated based on their ability to rescue proliferation in HIV-specific exhausted CD8 T-cells.

Figure 3:
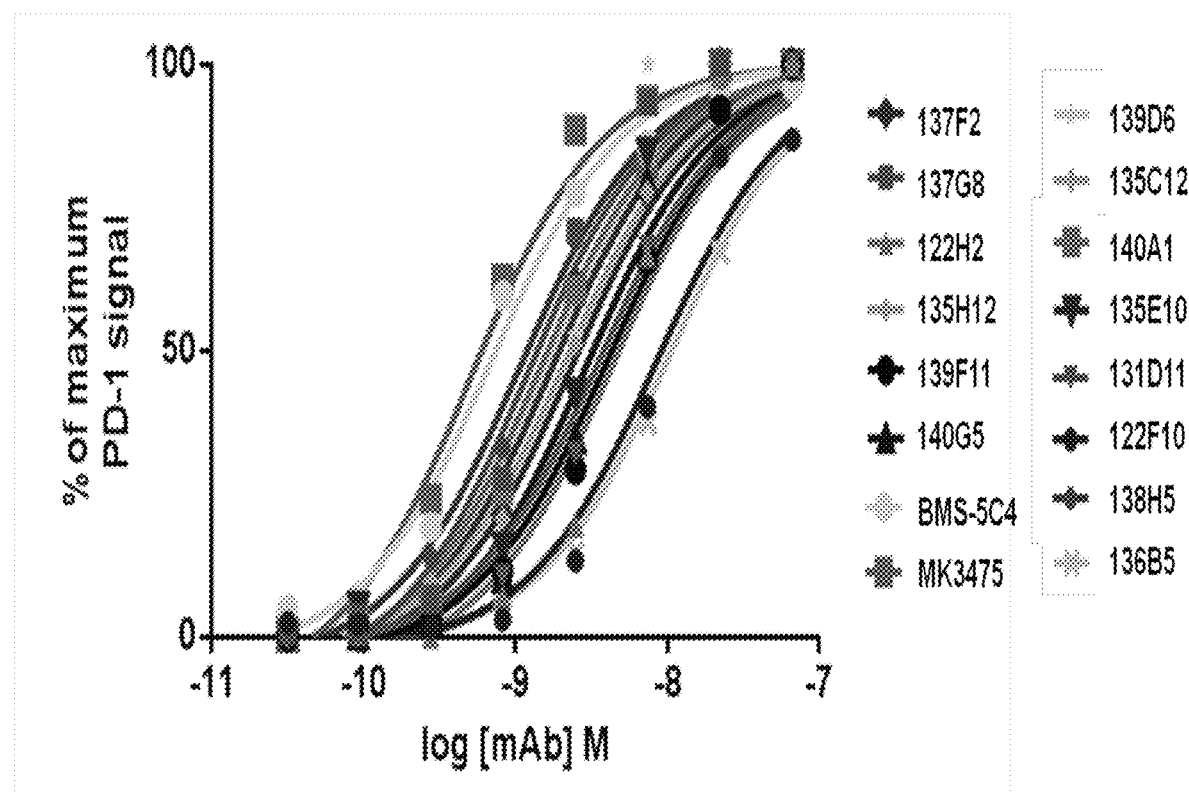
FIG. 3. Concentration response binding of anti-PD-1 antibodies to cell surface PD-1 on activated CD4 T-cells.

In a primary screen of antibody supernatants from individual cell cultured hybridoma cell clones, the EFRA assay was carried out to evaluate the functional effect of anti-PD1 antibodies on the proliferation of HIV-specific CD8 T cells (FIG. 2). Antibody clones in the upper box (E8-3, C2-3, E1-3, F3-3, H8-3, C10-2, G2-1, G3-2, H2-1, and H4-2) act as PD-1 antagonists and stimulate proliferation while antibody clones in the lower box (C8-1 and G10-2) are agonistic and promote the PD-1 negative regulatory effect. The level of proliferation induced by the peptide control (Pep 8) is indicated by the lower horizontal line (just below 1%) and the induced proliferation by the Merck MK-3475 anti-PD1 antibody is shown in the upper horizontal line (just above 2%). Antibodies of interest identified by these processes underwent a second round of subcloning and the resulting hybridoma clones were used for the production and purification of the antibodies in Table 2. Binding assays were carried out with the purified anti-PD-1 antibodies to ensure that the subclones retained their affinity for PD-1. The concentration response binding of anti-PD-1 antibodies to cell surface PD-1 was evaluated on activated CD4 T-cells (FIG. 3).

Figure 4:
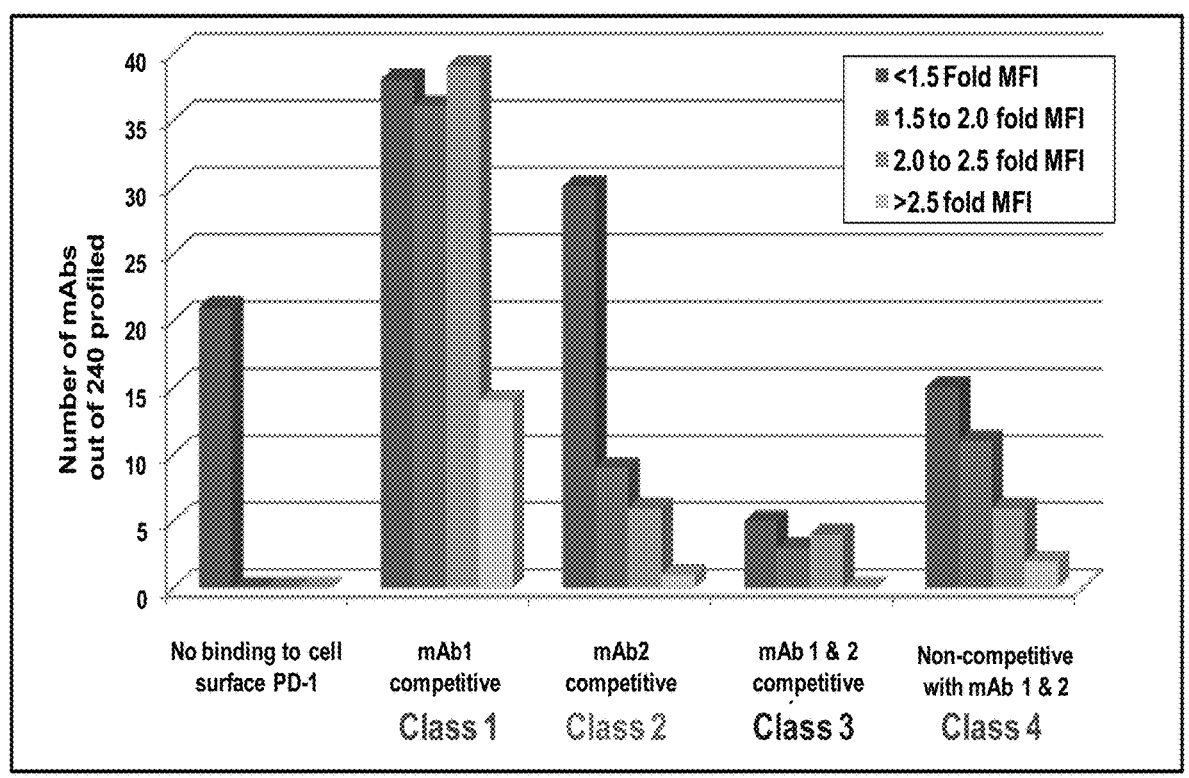
FIG. 4. Antibody classes.
Figure 5D:
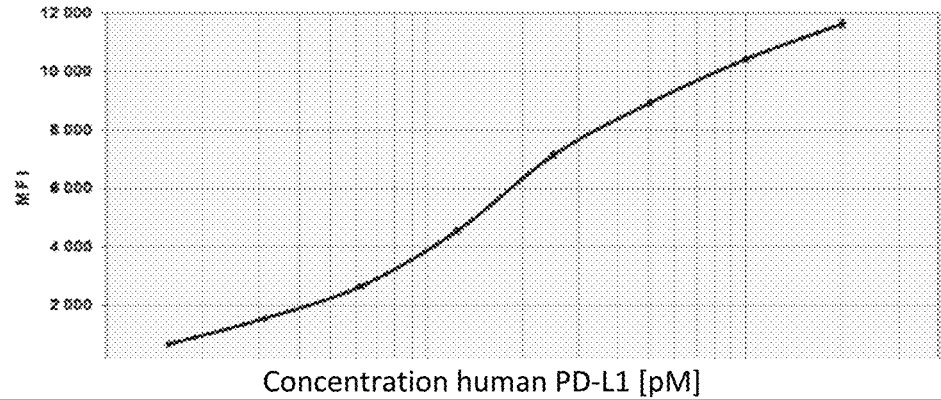
FIG. 5D. Class 1 mAb 137F2: strongly competitive.
Figure 5E:
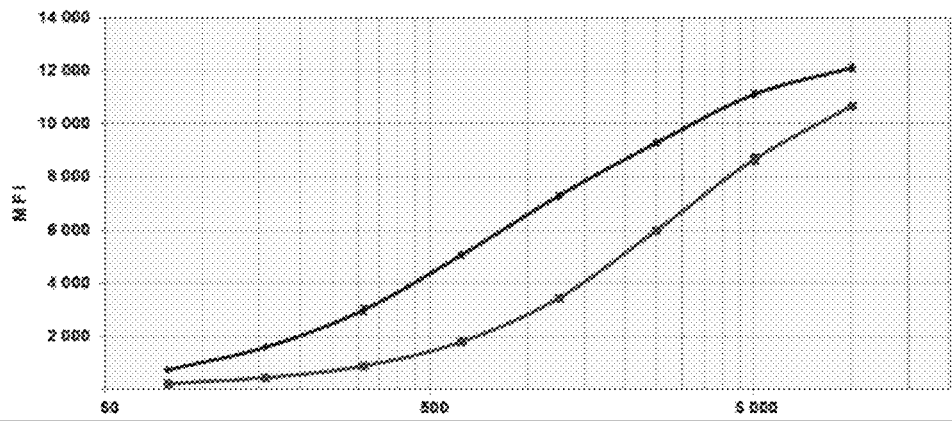
FIG. 5E. Class 1 mAb 132F7: partially competitive (IC50~200 pM; Imax=100%).
Figure 5F:
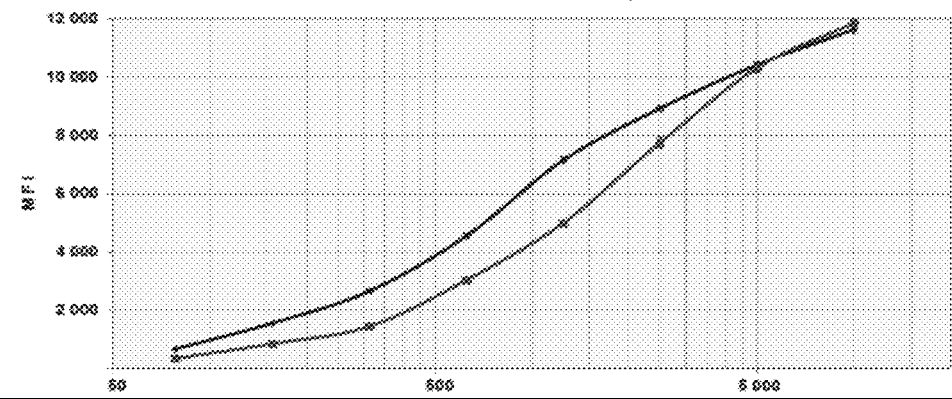
FIG. 5F. Class 1 mAb 136B4: non-competitive.
Figure 6A:
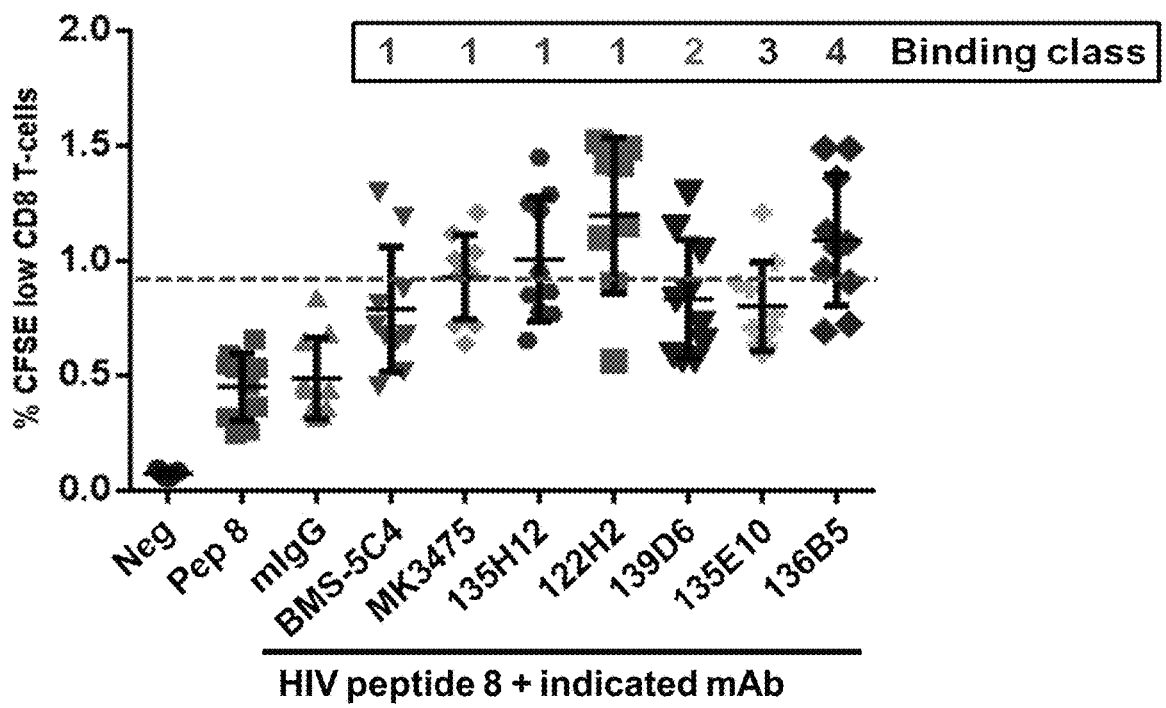
FIG. 6A. HIV peptide 8+BMS-5C4, MK3475, 135H12, 122H2, 139D6, 135E10, or 136B5.
Figure 6B:
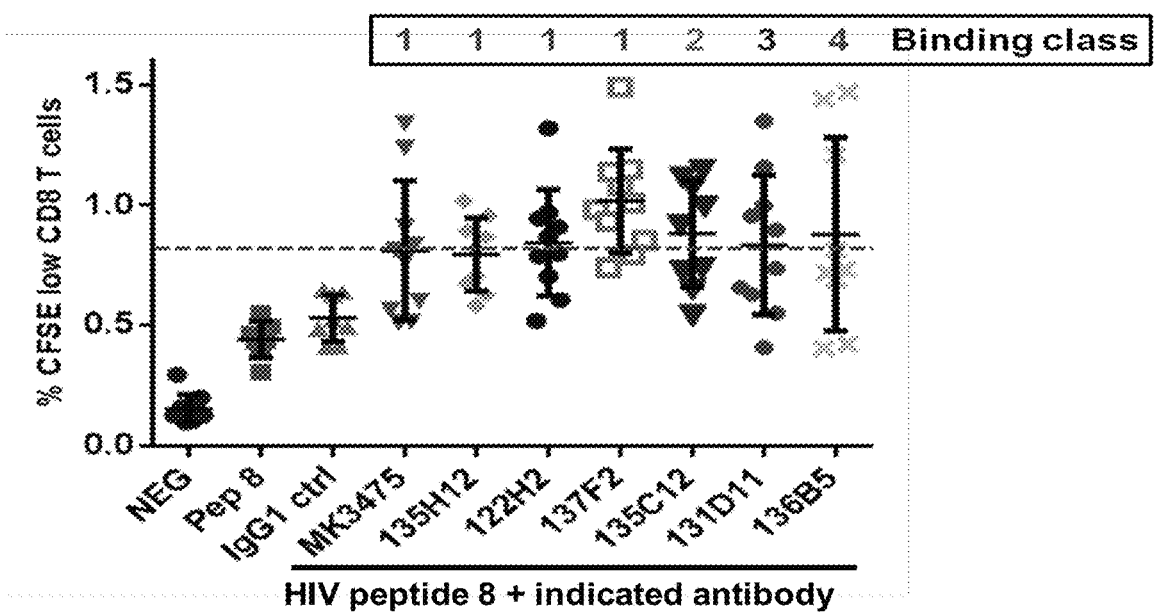
FIG. 6B. HIV peptide 8+MK3475, 135H12, 122H2, 137F2, 135C12, 135D11, or 136B5.
Figure 7:
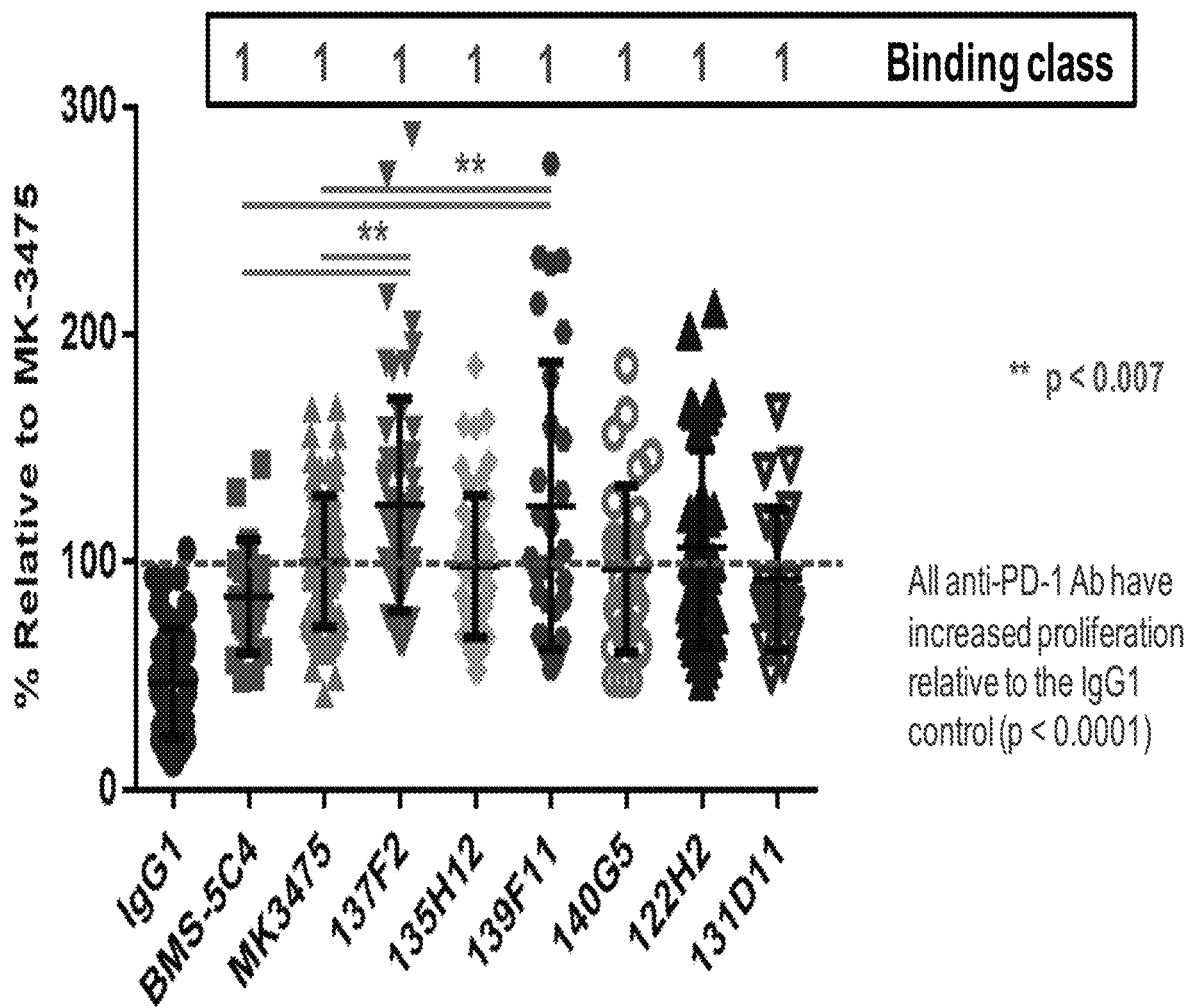
FIG. 7. Enhanced restoration of HIV peptide specific CD8 T-cell proliferation mediated by the combination of anti-PD-1 antibodies binding to different PD-1 epitopes in a functional exhaustion recovery assay.

The EFRA provides for the selection of binding agents that restore T-cells from functional exhaustion but are not necessarily antagonistic, meaning those binding agents that do not necessarily interfere with the interaction between PD-1 and its biological ligand(s) (e.g., PD-L1 or PD-L2). An embodiment of the EFRA was to identify such binding agents (antibodies) that bind PD-1. Epitope mapping of antibody binding to PD-1 was performed with two separate biochemical assays. In one assay, competitive binding to PD-1 Fc fusion protein labeled beads was evaluated between one of two commercial anti-PD-1 antibodies (BMS-5C4 and MK3475) and the anti-PD-1 antibodies listed (also described in Table 2). Four classes of monoclonal antibodies binding to distinct epitopes were identified based on this assay. These are: class 1 (competitive with the EH12.2H7 commercial monoclonal antibody clone that blocks the interaction of PD-1 with PD-L1), class 2 (competitive with the J116 commercial monoclonal antibody clone that binds PD-1 but does not effectively block the interaction of PD-1 with PD-L1), class 3 (competitive with both the EH12.2H7 and J116 commercial monoclonal antibodies), and class 4 (non-competitive with either the EH12.2H7 or J116 commercial antibodies). The relative binding of these antibodies for cell surface PD-1 is represented by the mean fluorescence intensity (MFI) relative to a control anti-PD-1 antibody in FIG. 4. These results show that tight binding antibodies were identified from all four binding classes. A second Luminex binding assay was used to directly evaluate if an anti-PD-1 antibody blocks the interaction between PD-1 and PD-L1. This assay was carried out using PD-1 Fc fusion protein coated beads that were incubated in the absence or presence of different concentrations of the anti-PD-1 antibodies listed in Table 2. A fixed concentration of biotinylated PD-L1, approximately equivalent to the $IC_{50}$ of the PD-1/PD-L1 interaction, was then incubated with the PD-1/antibody complex and PD-L1 binding was detected using fluorescently labeled streptavidin (representative binding curves shown in FIG. 5a-c). Using this biochemical assay, antibodies were defined as being competitive, partially competitive or non-competitive with the PD-1/PD-L1 interaction. The competitive, partially competitive and non-competitive antibodies were identified which bind distinct sites on PD-1 and exhibit high binding affinity (Table 2). Further evaluation of antibodies that bind PD-1 and are non-competitive or partially competitive with PD-L1 were performed by incubating PD-1 Fc fusion protein coated Luminex beads with 20 nM of an anti-PD-1 antibody from Table 2 followed by an incubation of the PD-1/antibody complex with different concentrations of biotinylated PD-L1. FIG. 5d-f shows that a competitive anti-PD-1 antibody completely blocks the interaction between PD-1 and PD-L1. Partially competitive and non-competitive anti-PD-1 antibodies listed in Table 2 results in a shift in the binding affinity of PD-L1 for PD-1, but does not block the interaction when concentration of PD-L1 are increased. Some of these antibodies were also shown to exhibit statistically significant increases in proliferation relative to controls (peptide 8 alone control or the peptide and IgG1 isotype control antibody in FIGS. 6a and 6b). Class 1 antibodies (competitive with the EH12.2H7 commercial monoclonal antibody that blocks the interaction of PD-1 with PD-L1) or competitive in the PD-1/PD-L1 intereaction assay were generally determined to provide improved proliferative restoration. In combining the data from multiple EFRA experiments and using MK-3475 as the common comparator, FIG. 7 shows that select antibodies described in Table 2 exhibited equivalent or statistically improved activity (p<0.007) compared to the benchmark MK-3475 antibody.

Example 2

Antibody Combinations

Figure 8:
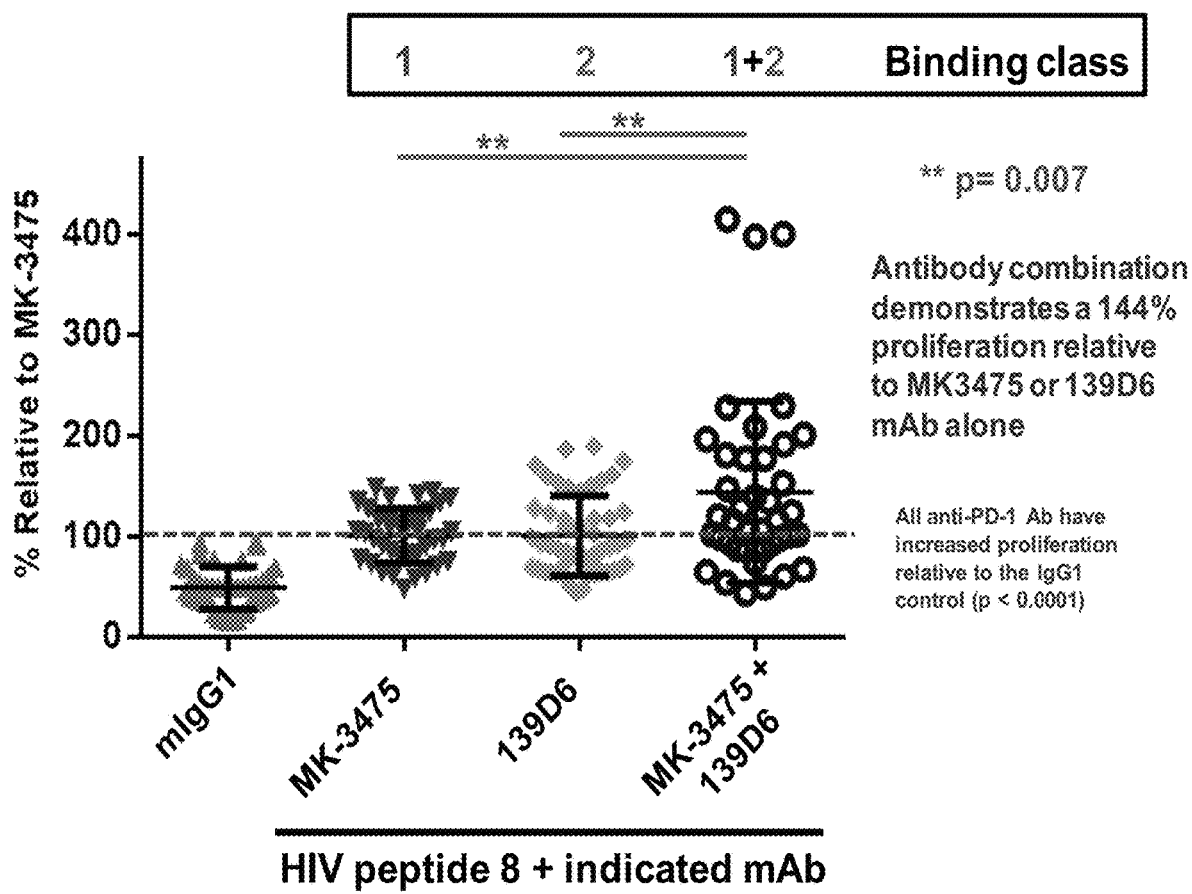
FIG. 8. Synergy between a first binding agent that blocks the interaction of PD-1 and PD-L1 with a second binding agent that does not block the interaction of PD-1 and PD-L1.

Combinations of antibodies binding to different PD-1 epitopes were found to enhance restoration of HIV peptide specific CD8 T-cell proliferation in a functional exhaustion recovery assay (FIG. 8). Synergy between antibody types was also observed. For instance, it was determined that class 1 (MK-3475 in FIG. 8) and class 2 (139D6 in FIG. 8) antibodies are able to simultaneously bind PD-1. While the maximum stimulation observed for MK-3475 is consistently about 200% relative to the HIV peptide, combinations of MK-3475 and 139D6 monoclonal antibodies at 5 µg/ml exhibited synergy with a 288% increase in HIV-specific CD8 T cell proliferation relative to the HIV peptide control alone or a 144% increased proliferation relative to MK-3475 or 139D6 added alone (FIG. 8). This synergistic increase in proliferation was observed in several experimental tests with a statistically significant p value of 0.007. As a comparison, addition of 10 µg/ml of either MK-3475 or 139D6 alone did not result in an increased proliferation in the EFRA. Thus, the combination of a first binding agent that blocks the interaction of PD-1 and PD-L1 with a second binding agent that does not block the interaction of PD-1 and PD-L1 has been determined to act synergistically to rescue T cells from exhaustion.

While certain embodiments have been described in terms of the preferred embodiments, it is understood that variations and modifications will occur to those skilled in the art. Therefore, it is intended that the appended claims cover all such equivalent variations that come within the scope of the following claims.

REFERENCES

1. Chun T W et al. *Nature* 387: 183-188, 1997
2. Chun T W et al. *Proc Natl Acad Sci USA* 94: 13193-13197, 1997
3. Finzi D et al. *Science* 278: 1295-1300, 1997
4. Chomont N et al. *Nat Med* 15:893-900, 2009
5. Siliciano J D et al. *Nat Med* 9:727-728, 203
6. Perreau M et al. *J Exp Med* 210: 143-156, 2013
7. Rong L and Perelson A *J Theoret Biol* 260:308-331, 2009
8. Sigal A et al. *Nature* 477:95-98, 2011
9. Katlama C et al. *Lancet* 381:2109-2117, 2013
10. Hansen S G et al. *Nature* 503:100-106, 2013
11. Klein F et al. *Nature* 492: 518.522, 2012
12. Barouch D H et al. *Nature* 503:224-228, 2013
13. Trautmann L et al. *Nat Med* 12:1198-1202, 2006
14. Day C L et al. *Nature* 443:350-354, 2006
15. Archin N M et al. *Nature* 487:482-485, 2012
16. Sievers E L and Senter P D *Annu Rev Med.* 64:15-29, 2013
17. Zolot R S et al. *Nat Rev Drug Discov* 4:259-260, 2013

---

What is claimed is:

1. A combination of binding agents, the combination comprising a first binding agent that does not block the interaction of PD-1 and PD-L1 and a second binding agent that blocks the interaction of PD-1 and PD-L1, wherein the first binding agent comprises:
- a VH comprising complementarity determining regions (CDRs) 1, 2, and 3 as set forth in SEQ ID NOS: 1, 24, and 47, respectively; and a VL comprising CDRs 1, 2, and 3 as set forth in SEQ ID NOS: 70, 93, and 116, respectively;
- a VH comprising complementarity determining regions (CDRs) 1, 2, and 3 as set forth in SEQ ID NOS: 2, 25, and 48, respectively; and a VL comprising CDRs 1, 2, and 3 as set forth in SEQ ID NOS: 71, 94, and 117, respectively;
- a VH comprising complementarity determining regions (CDRs) 1, 2, and 3 as set forth in SEQ ID NOS: 3, 26, and 49, respectively; and a VL comprising CDRs 1, 2, and 3 as set forth in SEQ ID NOS: 72, 95, and 118, respectively;
- a VH comprising complementarity determining regions (CDRs) 1, 2, and 3 as set forth in SEQ ID NOS: 5, 28, and 51, respectively; and a VL comprising CDRs 1, 2, and 3 as set forth in SEQ ID NOS: 74, 97, and 120, respectively;
- a VH comprising complementarity determining regions (CDRs) 1, 2, and 3 as set forth in SEQ ID NOS: 7, 30, and 53, respectively; and a VL comprising CDRs 1, 2, and 3 as set forth in SEQ ID NOS: 76, 99, and 122, respectively;
- a VH comprising complementarity determining regions (CDRs) 1, 2, and 3 as set forth in SEQ ID NOS: 13, 36, and 59, respectively; and a VL comprising CDRs 1, 2, and 3 as set forth in SEQ ID NOS: 82, 105, and 128, respectively;
- a VH comprising complementarity determining regions (CDRs) 1, 2, and 3 as set forth in SEQ ID NOS: 16, 39, and 62, respectively; and a VL comprising CDRs 1, 2, and 3 as set forth in SEQ ID NOS: 85, 108, and 131, respectively;
- a VH comprising complementarity determining regions (CDRs) 1, 2, and 3 as set forth in SEQ ID NOS: 17, 40, and 63, respectively; and a VL comprising CDRs 1, 2, and 3 as set forth in SEQ ID NOS: 86, 109, and 132, respectively;
- a VH comprising complementarity determining regions (CDRs) 1, 2, and 3 as set forth in SEQ ID NOS: 18, 41, and 64, respectively; and a VL comprising CDRs 1, 2, and 3 as set forth in SEQ ID NOS: 87, 110, and 133, respectively; or,
- a VH comprising complementarity determining regions (CDRs) 1, 2, and 3 as set forth in SEQ ID NOS: 19, 42, and 65, respectively; and a VL comprising CDRs 1, 2, and 3 as set forth in SEQ ID NOS: 88, 111, and 134, respectively.

2. The combination of claim 1 wherein the second binding agent is selected from the group consisting of:
- a VH comprising complementarity determining regions (CDRs) 1, 2, and 3 as set forth in SEQ ID NOS: 4, 27, and 50, respectively; and a VL comprising CDRs 1, 2, and 3 as set forth in SEQ ID NOS: 73, 96, and 119, respectively;
- a VH comprising complementarity determining regions (CDRs) 1, 2, and 3 as set forth in SEQ ID NOS: 6, 29, and 52, respectively; and a VL comprising CDRs 1, 2, and 3 as set forth in SEQ ID NOS: 75, 98, and 121, respectively;
- a VH comprising complementarity determining regions (CDRs) 1, 2, and 3 as set forth in SEQ ID NOS: 8, 31, and 54, respectively; and a VL comprising CDRs 1, 2, and 3 as set forth in SEQ ID NOS: 77, 100, and 123, respectively;
- a VH comprising complementarity determining regions (CDRs) 1, 2, and 3 as set forth in SEQ ID NOS: 9, 32, and 55, respectively; and a VL comprising CDRs 1, 2, and 3 as set forth in SEQ ID NOS: 78, 101, and 124, respectively;
- a VH comprising complementarity determining regions (CDRs) 1, 2, and 3 as set forth in SEQ ID NOS: 10, 33, and 56, respectively; and a VL comprising CDRs 1, 2, and 3 as set forth in SEQ ID NOS: 79, 102, and 125, respectively;
- a VH comprising complementarity determining regions (CDRs) 1, 2, and 3 as set forth in SEQ ID NOS: 11, 34, and 57, respectively; and a VL comprising CDRs 1, 2, and 3 as set forth in SEQ ID NOS: 80, 103, and 126, respectively;
- a VH comprising complementarity determining regions (CDRs) 1, 2, and 3 as set forth in SEQ ID NOS: 12, 35, and 58, respectively; and a VL comprising CDRs 1, 2, and 3 as set forth in SEQ ID NOS: 81, 104, and 127, respectively;
- a VH comprising complementarity determining regions (CDRs) 1, 2, and 3 as set forth in SEQ ID NOS: 14, 37, and 60, respectively; and a VL comprising CDRs 1, 2, and 3 as set forth in SEQ ID NOS: 83, 106, and 129, respectively;
- a VH comprising complementarity determining regions (CDRs) 1, 2, and 3 as set forth in SEQ ID NOS: 20, 43, and 66, respectively; and a VL comprising CDRs 1, 2, and 3 as set forth in SEQ ID NOS: 89, 112, and 135, respectively;
- a VH comprising complementarity determining regions (CDRs) 1, 2, and 3 as set forth in SEQ ID NOS: 21, 44, and 67, respectively; and a VL comprising CDRs 1, 2, and 3 as set forth in SEQ ID NOS: 90, 113, and 136, respectively;
- a VH comprising complementarity determining regions (CDRs) 1, 2, and 3 as set forth in SEQ ID NOS: 22, 45, and 68, respectively; and a VL comprising CDRs 1, 2, and 3 as set forth in SEQ ID NOS: 91, 114, and 137, respectively;
- a VH comprising complementarity determining regions (CDRs) 1, 2, and 3 as set forth in SEQ ID NOS: 23, 46, and 69, respectively; and a VL comprising CDRs 1, 2, and 3 as set forth in SEQ ID NOS: 92, 115, 138, respectively; and,
- pembrolizumab.

3. The combination of claim 1 wherein the first and/or second binding agents are monoclonal antibodies.

4. The combination of claim 1 wherein the first and/or second binding agents are human antibodies, canine antibodies, chicken antibodies, goat antibodies, mouse antibodies, pig antibodies, or rat antibodies.

5. The combination of claim 1 wherein the first and/or second binding agents are selected from the group consisting of an $F_{ab}$, $F_{(ab')}2$, $F_{ab'}$, single chain antibody, $F_v$, single domain antibody, mono-specific antibody, bi-specific antibody, tri-specific antibody, multi-valent antibody, chimeric antibody, canine-human chimeric antibody, canine-mouse chimeric antibody, antibody comprising a canine Fc, humanized antibody, human antibody, caninized antibody, CDR-grafted antibody, shark antibody, nanobody, camelid antibody, microbody, intrabody, and derivative thereof.

6. The combination of claim 1 wherein the first binding agent comprises a VH comprising complementarity determining regions (CDRs) 1, 2, and 3 as set forth in SEQ ID NOS: 17, 40, and 63, respectively; and a VL comprising CDRs 1, 2, and 3 as set forth in SEQ ID NOS: 86, 109, and 132, respectively; and the second binding agent is pembrolizumab.

7. A composition comprising the combination of claim 1 and at least one pharmaceutically acceptable carrier.

8. A composition comprising the combination of claim 2 and at least one pharmaceutically acceptable carrier.

9. A composition comprising the combination of claim 6 and at least one pharmaceutically acceptable carrier.

* * * * *

SEQUENCE LISTING

```
<160> NUMBER OF SEQ ID NOS: 138

<210> SEQ ID NO 1
<211> LENGTH: 5
<212> TYPE: PRT
<213> ORGANISM: Homo sapiens

<400> SEQUENCE: 1

Asp Asp Phe Leu His
1               5

<210> SEQ ID NO 2
<211> LENGTH: 5
<212> TYPE: PRT
<213> ORGANISM: Homo sapiens

<400> SEQUENCE: 2

Asn Tyr Tyr Ile His
1               5

<210> SEQ ID NO 3
<211> LENGTH: 5
<212> TYPE: PRT
<213> ORGANISM: Homo sapiens
```

```
<400> SEQUENCE: 3

Asn Tyr Tyr Ile His
1               5

<210> SEQ ID NO 4
<211> LENGTH: 5
<212> TYPE: PRT
<213> ORGANISM: Homo sapiens

<400> SEQUENCE: 4

Ser Asn Trp Met His
1               5

<210> SEQ ID NO 5
<211> LENGTH: 5
<212> TYPE: PRT
<213> ORGANISM: Homo sapiens

<400> SEQUENCE: 5

Arg Tyr Trp Met His
1               5

<210> SEQ ID NO 6
<211> LENGTH: 5
<212> TYPE: PRT
<213> ORGANISM: Homo sapiens

<400> SEQUENCE: 6

Ser Asn Trp Met His
1               5

<210> SEQ ID NO 7
<211> LENGTH: 5
<212> TYPE: PRT
<213> ORGANISM: Homo sapiens

<400> SEQUENCE: 7

Asn Ser Tyr Ile His
1               5

<210> SEQ ID NO 8
<211> LENGTH: 5
<212> TYPE: PRT
<213> ORGANISM: Homo sapiens

<400> SEQUENCE: 8

Asn Tyr Trp Ile Gly
1               5

<210> SEQ ID NO 9
<211> LENGTH: 5
<212> TYPE: PRT
<213> ORGANISM: Homo sapiens

<400> SEQUENCE: 9

Ser Tyr Ala Met Ser
1               5

<210> SEQ ID NO 10
<211> LENGTH: 6
<212> TYPE: PRT
<213> ORGANISM: Homo sapiens
```

```
<400> SEQUENCE: 10

Ser Asp Tyr Ala Trp Asn
1               5

<210> SEQ ID NO 11
<211> LENGTH: 5
<212> TYPE: PRT
<213> ORGANISM: Homo sapiens

<400> SEQUENCE: 11

Ser Tyr Trp Ile Asn
1               5

<210> SEQ ID NO 12
<211> LENGTH: 5
<212> TYPE: PRT
<213> ORGANISM: Homo sapiens

<400> SEQUENCE: 12

Ser Ser Tyr Ile His
1               5

<210> SEQ ID NO 13
<211> LENGTH: 5
<212> TYPE: PRT
<213> ORGANISM: Homo sapiens

<400> SEQUENCE: 13

Asn His Gly Met Ser
1               5

<210> SEQ ID NO 14
<211> LENGTH: 5
<212> TYPE: PRT
<213> ORGANISM: Homo sapiens

<400> SEQUENCE: 14

Asn Tyr Trp Ile Gly
1               5

<210> SEQ ID NO 15
<211> LENGTH: 5
<212> TYPE: PRT
<213> ORGANISM: Homo sapiens

<400> SEQUENCE: 15

Asp Ser Tyr Ile His
1               5

<210> SEQ ID NO 16
<211> LENGTH: 5
<212> TYPE: PRT
<213> ORGANISM: Homo sapiens

<400> SEQUENCE: 16

Asp Thr Tyr Ile His
1               5

<210> SEQ ID NO 17
<211> LENGTH: 5
<212> TYPE: PRT
<213> ORGANISM: Homo sapiens
```

```
<400> SEQUENCE: 17

Asn Phe Tyr Ile His
1               5

<210> SEQ ID NO 18
<211> LENGTH: 5
<212> TYPE: PRT
<213> ORGANISM: Homo sapiens

<400> SEQUENCE: 18

Asp Ser Tyr Ile His
1               5

<210> SEQ ID NO 19
<211> LENGTH: 5
<212> TYPE: PRT
<213> ORGANISM: Homo sapiens

<400> SEQUENCE: 19

Asp Asp Phe Leu His
1               5

<210> SEQ ID NO 20
<211> LENGTH: 5
<212> TYPE: PRT
<213> ORGANISM: Homo sapiens

<400> SEQUENCE: 20

Ser Tyr Phe Met Ser
1               5

<210> SEQ ID NO 21
<211> LENGTH: 5
<212> TYPE: PRT
<213> ORGANISM: Homo sapiens

<400> SEQUENCE: 21

Asn His Gly Met Ser
1               5

<210> SEQ ID NO 22
<211> LENGTH: 5
<212> TYPE: PRT
<213> ORGANISM: Homo sapiens

<400> SEQUENCE: 22

Asn Tyr Trp Ile Gly
1               5

<210> SEQ ID NO 23
<211> LENGTH: 5
<212> TYPE: PRT
<213> ORGANISM: Homo sapiens

<400> SEQUENCE: 23

Ser Phe Ala Met Ser
1               5

<210> SEQ ID NO 24
<211> LENGTH: 17
<212> TYPE: PRT
<213> ORGANISM: Homo sapiens
```

<400> SEQUENCE: 24

Arg Ile Asp Pro Ala Asn Gly Glu Ser Arg Tyr Ala Pro Lys Phe Gln
1               5                   10                  15

Asp

<210> SEQ ID NO 25
<211> LENGTH: 17
<212> TYPE: PRT
<213> ORGANISM: Homo sapiens

<400> SEQUENCE: 25

Ser Ile Tyr Pro Asn Tyr Gly Asp Thr Asn Tyr Asn Gln Lys Val Lys
1               5                   10                  15

Asp

<210> SEQ ID NO 26
<211> LENGTH: 17
<212> TYPE: PRT
<213> ORGANISM: Homo sapiens

<400> SEQUENCE: 26

Ser Ile Tyr Pro Asn Tyr Gly Glu Thr Asn Tyr Asn Gln Glu Phe Lys
1               5                   10                  15

Gly

<210> SEQ ID NO 27
<211> LENGTH: 17
<212> TYPE: PRT
<213> ORGANISM: Homo sapiens

<400> SEQUENCE: 27

Ala Val Asn Pro Gly Asn Ser Asp Thr Thr Tyr Asn Gln Lys Phe Lys
1               5                   10                  15

Gly

<210> SEQ ID NO 28
<211> LENGTH: 17
<212> TYPE: PRT
<213> ORGANISM: Homo sapiens

<400> SEQUENCE: 28

Asn Ile Asp Pro Ser Asp Ser Thr Thr His Tyr Asn Pro Lys Phe Arg
1               5                   10                  15

Asp

<210> SEQ ID NO 29
<211> LENGTH: 17
<212> TYPE: PRT
<213> ORGANISM: Homo sapiens

<400> SEQUENCE: 29

Ala Val Tyr Pro Gly Asn Ser Asp Thr Thr Tyr Asn Gln Asn Phe Lys
1               5                   10                  15

Gly

<210> SEQ ID NO 30
<211> LENGTH: 17
<212> TYPE: PRT
<213> ORGANISM: Homo sapiens

```
<400> SEQUENCE: 30

Trp Ile Ser Pro Gly Asp Gly Ser Thr Asn Tyr Asn Glu Lys Phe Lys
1               5                   10                  15
Gly

<210> SEQ ID NO 31
<211> LENGTH: 17
<212> TYPE: PRT
<213> ORGANISM: Homo sapiens

<400> SEQUENCE: 31

Asp Ile Tyr Pro Gly Gly Gly Tyr Thr Asn Tyr Asn Glu Lys Phe Lys
1               5                   10                  15
Gly

<210> SEQ ID NO 32
<211> LENGTH: 17
<212> TYPE: PRT
<213> ORGANISM: Homo sapiens

<400> SEQUENCE: 32

Thr Ile Ser Gly Gly Gly Ala Asp Thr Tyr Tyr Leu Asp Asn Val Lys
1               5                   10                  15
Gly

<210> SEQ ID NO 33
<211> LENGTH: 16
<212> TYPE: PRT
<213> ORGANISM: Homo sapiens

<400> SEQUENCE: 33

Tyr Ile Asn Tyr Ser Gly Tyr Thr Asn Tyr Asn Pro Phe Leu Lys Ser
1               5                   10                  15

<210> SEQ ID NO 34
<211> LENGTH: 17
<212> TYPE: PRT
<213> ORGANISM: Homo sapiens

<400> SEQUENCE: 34

Asn Ile Tyr Pro Gly Ser Ser Ser Thr Asp Tyr Asn Glu Lys Phe Lys
1               5                   10                  15
Ser

<210> SEQ ID NO 35
<211> LENGTH: 17
<212> TYPE: PRT
<213> ORGANISM: Homo sapiens

<400> SEQUENCE: 35

Trp Ile Phe Pro Gly Asp Gly Lys Thr Asn Tyr Asn Glu Lys Phe Arg
1               5                   10                  15
Asp

<210> SEQ ID NO 36
<211> LENGTH: 17
<212> TYPE: PRT
<213> ORGANISM: Homo sapiens
```

```
<400> SEQUENCE: 36

Ser Ile Asn Thr Gly Gly Tyr Ser Thr Tyr Tyr Pro Asp Asn Val Lys
1               5                   10                  15
Gly

<210> SEQ ID NO 37
<211> LENGTH: 17
<212> TYPE: PRT
<213> ORGANISM: Homo sapiens

<400> SEQUENCE: 37

Asp Ile Tyr Pro Gly Ser Glu Tyr Glu Asn Tyr Asn Glu Lys Phe Lys
1               5                   10                  15
Gly

<210> SEQ ID NO 38
<211> LENGTH: 17
<212> TYPE: PRT
<213> ORGANISM: Homo sapiens

<400> SEQUENCE: 38

Arg Ile Asp Pro Ala His Gly Asn Val Ile Tyr Ala Ser Lys Phe Arg
1               5                   10                  15
Asp

<210> SEQ ID NO 39
<211> LENGTH: 17
<212> TYPE: PRT
<213> ORGANISM: Homo sapiens

<400> SEQUENCE: 39

Arg Ile Asp Leu Ala Asn Asp Asp Ile Leu Tyr Ala Ser Lys Phe Gln
1               5                   10                  15
Gly

<210> SEQ ID NO 40
<211> LENGTH: 17
<212> TYPE: PRT
<213> ORGANISM: Homo sapiens

<400> SEQUENCE: 40

Ser Ile Tyr Pro Asn Tyr Gly Asp Thr Ala Tyr Asn Gln Lys Phe Lys
1               5                   10                  15
Asp

<210> SEQ ID NO 41
<211> LENGTH: 17
<212> TYPE: PRT
<213> ORGANISM: Homo sapiens

<400> SEQUENCE: 41

Arg Ile Asp Pro Ala Arg Asp Asn Ile Ile Tyr Ala Ser Lys Phe Arg
1               5                   10                  15
Asp

<210> SEQ ID NO 42
<211> LENGTH: 17
<212> TYPE: PRT
<213> ORGANISM: Homo sapiens
```

-continued

```
<400> SEQUENCE: 42

Arg Ile Asp Pro Ala Asn Gly Glu Ser Arg Tyr Ala Pro Gln Phe Gln
1               5                   10                  15

Asp

<210> SEQ ID NO 43
<211> LENGTH: 17
<212> TYPE: PRT
<213> ORGANISM: Homo sapiens

<400> SEQUENCE: 43

Gly Ile Ser Thr Gly Gly Ala Asp Thr Tyr Tyr Ala Asp Ser Met Lys
1               5                   10                  15

Gly

<210> SEQ ID NO 44
<211> LENGTH: 17
<212> TYPE: PRT
<213> ORGANISM: Homo sapiens

<400> SEQUENCE: 44

Ser Ile Ser Gly Gly Gly Asp Asn Thr Tyr Tyr Pro Asp Asn Leu Lys
1               5                   10                  15

Gly

<210> SEQ ID NO 45
<211> LENGTH: 17
<212> TYPE: PRT
<213> ORGANISM: Homo sapiens

<400> SEQUENCE: 45

Asp Ile Tyr Pro Gly Gly Asp His Lys Asn Tyr Asn Glu Lys Phe Lys
1               5                   10                  15

Asp

<210> SEQ ID NO 46
<211> LENGTH: 17
<212> TYPE: PRT
<213> ORGANISM: Homo sapiens

<400> SEQUENCE: 46

Thr Ile Thr Gly Gly Gly Val Asn Thr Tyr Tyr Pro Asp Thr Val Lys
1               5                   10                  15

Gly

<210> SEQ ID NO 47
<211> LENGTH: 12
<212> TYPE: PRT
<213> ORGANISM: Homo sapiens

<400> SEQUENCE: 47

Thr Asp Tyr Arg Gly Tyr Tyr Tyr Ala Met Asp Tyr
1               5                   10

<210> SEQ ID NO 48
<211> LENGTH: 8
<212> TYPE: PRT
<213> ORGANISM: Homo sapiens
```

<400> SEQUENCE: 48

Gly Tyr Ser Tyr Ala Met Asp Tyr
1               5

<210> SEQ ID NO 49
<211> LENGTH: 8
<212> TYPE: PRT
<213> ORGANISM: Homo sapiens

<400> SEQUENCE: 49

Gly Tyr Ser Tyr Ala Met Asp Tyr
1               5

<210> SEQ ID NO 50
<211> LENGTH: 10
<212> TYPE: PRT
<213> ORGANISM: Homo sapiens

<400> SEQUENCE: 50

Gly Arg Ser Tyr Asp Gly Ser Phe Asp Tyr
1               5                   10

<210> SEQ ID NO 51
<211> LENGTH: 15
<212> TYPE: PRT
<213> ORGANISM: Homo sapiens

<400> SEQUENCE: 51

Asp Leu Asp Asp Phe Tyr Val Gly Ser His Glu Asp Phe Asp Tyr
1               5                   10                  15

<210> SEQ ID NO 52
<211> LENGTH: 10
<212> TYPE: PRT
<213> ORGANISM: Homo sapiens

<400> SEQUENCE: 52

Gly Arg Ser Tyr Asp Gly Ser Phe Asp Tyr
1               5                   10

<210> SEQ ID NO 53
<211> LENGTH: 8
<212> TYPE: PRT
<213> ORGANISM: Homo sapiens

<400> SEQUENCE: 53

Glu Glu Tyr Asp Tyr Asp Asn Tyr
1               5

<210> SEQ ID NO 54
<211> LENGTH: 8
<212> TYPE: PRT
<213> ORGANISM: Homo sapiens

<400> SEQUENCE: 54

Gly Tyr Asp Phe Val Leu Asp Arg
1               5

<210> SEQ ID NO 55
<211> LENGTH: 9
<212> TYPE: PRT
<213> ORGANISM: Homo sapiens

```
<400> SEQUENCE: 55

Gln Arg Gly Glu Asn Leu Phe Ala His
1               5

<210> SEQ ID NO 56
<211> LENGTH: 11
<212> TYPE: PRT
<213> ORGANISM: Homo sapiens

<400> SEQUENCE: 56

Tyr Gly Gly Ser Tyr Pro Trp Asn Phe Asp Val
1               5                   10

<210> SEQ ID NO 57
<211> LENGTH: 8
<212> TYPE: PRT
<213> ORGANISM: Homo sapiens

<400> SEQUENCE: 57

Gly Leu Tyr Trp Tyr Phe Asp Val
1               5

<210> SEQ ID NO 58
<211> LENGTH: 8
<212> TYPE: PRT
<213> ORGANISM: Homo sapiens

<400> SEQUENCE: 58

Asn Asp Phe Asp Arg Gly Val Tyr
1               5

<210> SEQ ID NO 59
<211> LENGTH: 8
<212> TYPE: PRT
<213> ORGANISM: Homo sapiens

<400> SEQUENCE: 59

Asp Asp Tyr Asn Trp Phe Ala Tyr
1               5

<210> SEQ ID NO 60
<211> LENGTH: 8
<212> TYPE: PRT
<213> ORGANISM: Homo sapiens

<400> SEQUENCE: 60

Gly Tyr Asp Phe Val Leu Asp His
1               5

<210> SEQ ID NO 61
<211> LENGTH: 10
<212> TYPE: PRT
<213> ORGANISM: Homo sapiens

<400> SEQUENCE: 61

Ile Tyr Tyr Asp Tyr Gly Glu Gly Asp Phe
1               5                   10

<210> SEQ ID NO 62
<211> LENGTH: 10
<212> TYPE: PRT
<213> ORGANISM: Homo sapiens
```

<400> SEQUENCE: 62

Ile Tyr Tyr Asp Tyr Gly Glu Gly Asp Tyr
1               5                   10

<210> SEQ ID NO 63
<211> LENGTH: 8
<212> TYPE: PRT
<213> ORGANISM: Homo sapiens

<400> SEQUENCE: 63

Gly Tyr Ser Tyr Ala Met Asp Tyr
1               5

<210> SEQ ID NO 64
<211> LENGTH: 10
<212> TYPE: PRT
<213> ORGANISM: Homo sapiens

<400> SEQUENCE: 64

Ile Tyr Tyr Asp Tyr Gly Glu Gly Asp Tyr
1               5                   10

<210> SEQ ID NO 65
<211> LENGTH: 12
<212> TYPE: PRT
<213> ORGANISM: Homo sapiens

<400> SEQUENCE: 65

Thr Asp Tyr Arg Gly Tyr Tyr Tyr Ala Met Asp Tyr
1               5                   10

<210> SEQ ID NO 66
<211> LENGTH: 12
<212> TYPE: PRT
<213> ORGANISM: Homo sapiens

<400> SEQUENCE: 66

Leu Ser His Tyr Tyr Asp Gly Ile Pro Leu Asp Cys
1               5                   10

<210> SEQ ID NO 67
<211> LENGTH: 13
<212> TYPE: PRT
<213> ORGANISM: Homo sapiens

<400> SEQUENCE: 67

Val Arg Gln Leu Gly Leu His Arg Ala Ala Met Asp Tyr
1               5                   10

<210> SEQ ID NO 68
<211> LENGTH: 8
<212> TYPE: PRT
<213> ORGANISM: Homo sapiens

<400> SEQUENCE: 68

Gly Phe Asp Phe Val Leu Asp Tyr
1               5

<210> SEQ ID NO 69
<211> LENGTH: 12
<212> TYPE: PRT
<213> ORGANISM: Homo sapiens

<400> SEQUENCE: 69

Gln Ala Ile Tyr Asp Gly His Tyr Val Leu Asp Tyr
1               5                   10

<210> SEQ ID NO 70
<211> LENGTH: 17
<212> TYPE: PRT
<213> ORGANISM: Homo sapiens

<400> SEQUENCE: 70

Lys Ser Ser Gln Ser Val Leu Tyr Ser Ser Asn Gln Lys Asn Tyr Leu
1               5                   10                  15

Ala

<210> SEQ ID NO 71
<211> LENGTH: 11
<212> TYPE: PRT
<213> ORGANISM: Homo sapiens

<400> SEQUENCE: 71

Ser Ala Ser Gln Gly Ile Ser Asp Gly Leu Asn
1               5                   10

<210> SEQ ID NO 72
<211> LENGTH: 11
<212> TYPE: PRT
<213> ORGANISM: Homo sapiens

<400> SEQUENCE: 72

Ser Ala Ser Gln Gly Ile Ser Asn Gly Leu Asn
1               5                   10

<210> SEQ ID NO 73
<211> LENGTH: 11
<212> TYPE: PRT
<213> ORGANISM: Homo sapiens

<400> SEQUENCE: 73

Lys Ala Ser Gln Asp Ile Asn Lys Tyr Ile Ala
1               5                   10

<210> SEQ ID NO 74
<211> LENGTH: 16
<212> TYPE: PRT
<213> ORGANISM: Homo sapiens

<400> SEQUENCE: 74

Arg Ser Ser Gln Ser Ile Val Tyr Ser Asn Gly Asn Thr Tyr Leu Glu
1               5                   10                  15

<210> SEQ ID NO 75
<211> LENGTH: 11
<212> TYPE: PRT
<213> ORGANISM: Homo sapiens

<400> SEQUENCE: 75

Lys Ala Ser Gln Asp Ile Asn Lys Tyr Met Ala
1               5                   10

<210> SEQ ID NO 76
<211> LENGTH: 11
<212> TYPE: PRT
<213> ORGANISM: Homo sapiens

```
<400> SEQUENCE: 76

Lys Ala Ser Gln Asn Val Gly Thr Asn Val Gly
1               5                   10

<210> SEQ ID NO 77
<211> LENGTH: 17
<212> TYPE: PRT
<213> ORGANISM: Homo sapiens

<400> SEQUENCE: 77

Lys Ser Ser Gln Ser Leu Phe Asn Ser Glu Thr Gln Lys Asn Tyr Leu
1               5                   10                  15

Ala

<210> SEQ ID NO 78
<211> LENGTH: 11
<212> TYPE: PRT
<213> ORGANISM: Homo sapiens

<400> SEQUENCE: 78

Leu Ala Ser Gln Thr Ile Gly Thr Trp Leu Ala
1               5                   10

<210> SEQ ID NO 79
<211> LENGTH: 16
<212> TYPE: PRT
<213> ORGANISM: Homo sapiens

<400> SEQUENCE: 79

Arg Ser Ser Gln Thr Ile Val His Asn Asn Gly Asp Thr Tyr Leu Glu
1               5                   10                  15

<210> SEQ ID NO 80
<211> LENGTH: 17
<212> TYPE: PRT
<213> ORGANISM: Homo sapiens

<400> SEQUENCE: 80

Lys Ser Ser Gln Ser Leu Phe Asn Ser Gly Thr Arg Lys Asn Tyr Leu
1               5                   10                  15

Ala

<210> SEQ ID NO 81
<211> LENGTH: 11
<212> TYPE: PRT
<213> ORGANISM: Homo sapiens

<400> SEQUENCE: 81

Lys Ala Ser Gln Asn Val Asp Thr Asn Val Ala
1               5                   10

<210> SEQ ID NO 82
<211> LENGTH: 17
<212> TYPE: PRT
<213> ORGANISM: Homo sapiens

<400> SEQUENCE: 82

Lys Ser Ser Gln Ser Leu Leu Asn Ser Gly Asn Gln Lys Asn Tyr Leu
1               5                   10                  15

Thr
```

```
<210> SEQ ID NO 83
<211> LENGTH: 17
<212> TYPE: PRT
<213> ORGANISM: Homo sapiens

<400> SEQUENCE: 83

Lys Ser Ser Gln Ser Leu Phe Asn Ser Gly Thr Arg Lys Ser Tyr Leu
1               5                   10                  15

Ala

<210> SEQ ID NO 84
<211> LENGTH: 11
<212> TYPE: PRT
<213> ORGANISM: Homo sapiens

<400> SEQUENCE: 84

His Ala Ser Gln Asn Ile Asn Val Trp Leu Ser
1               5                   10

<210> SEQ ID NO 85
<211> LENGTH: 11
<212> TYPE: PRT
<213> ORGANISM: Homo sapiens

<400> SEQUENCE: 85

His Ala Ser Gln Asn Ile Asn Val Trp Leu Ser
1               5                   10

<210> SEQ ID NO 86
<211> LENGTH: 11
<212> TYPE: PRT
<213> ORGANISM: Homo sapiens

<400> SEQUENCE: 86

Ser Ala Ser Gln Gly Ile Ser Gly Asp Leu Asn
1               5                   10

<210> SEQ ID NO 87
<211> LENGTH: 11
<212> TYPE: PRT
<213> ORGANISM: Homo sapiens

<400> SEQUENCE: 87

His Ala Ser Gln Asn Ile Asn Val Trp Leu Ser
1               5                   10

<210> SEQ ID NO 88
<211> LENGTH: 17
<212> TYPE: PRT
<213> ORGANISM: Homo sapiens

<400> SEQUENCE: 88

Lys Ser Ser Gln Ser Val Leu Tyr Ser Ser Asn Gln Lys Asn Tyr Leu
1               5                   10                  15

Ala

<210> SEQ ID NO 89
<211> LENGTH: 15
<212> TYPE: PRT
<213> ORGANISM: Homo sapiens

<400> SEQUENCE: 89

Arg Ala Ser Glu Ser Val Asp Asn Ser Gly Val Ser Phe Leu Thr
1               5                   10                  15
```

```
<210> SEQ ID NO 90
<211> LENGTH: 11
<212> TYPE: PRT
<213> ORGANISM: Homo sapiens

<400> SEQUENCE: 90

Lys Ala Ser Gln Ser Val Ser Asp Asp Val Ser
1               5                   10

<210> SEQ ID NO 91
<211> LENGTH: 17
<212> TYPE: PRT
<213> ORGANISM: Homo sapiens

<400> SEQUENCE: 91

Lys Ser Ser Gln Ser Leu Phe Asn Ser Gly Thr Arg Lys Asn Tyr Leu
1               5                   10                  15

Ala

<210> SEQ ID NO 92
<211> LENGTH: 11
<212> TYPE: PRT
<213> ORGANISM: Homo sapiens

<400> SEQUENCE: 92

Arg Thr Ser Gly Asn Ile His Asn Tyr Leu Ala
1               5                   10

<210> SEQ ID NO 93
<211> LENGTH: 7
<212> TYPE: PRT
<213> ORGANISM: Homo sapiens

<400> SEQUENCE: 93

Trp Ala Ser Thr Arg Glu Ser
1               5

<210> SEQ ID NO 94
<211> LENGTH: 7
<212> TYPE: PRT
<213> ORGANISM: Homo sapiens

<400> SEQUENCE: 94

His Thr Ser Thr Leu His Ser
1               5

<210> SEQ ID NO 95
<211> LENGTH: 7
<212> TYPE: PRT
<213> ORGANISM: Homo sapiens

<400> SEQUENCE: 95

His Thr Ser Thr Leu His Ser
1               5

<210> SEQ ID NO 96
<211> LENGTH: 7
<212> TYPE: PRT
<213> ORGANISM: Homo sapiens

<400> SEQUENCE: 96

Tyr Thr Ser Thr Leu Arg Pro
1               5
```

<210> SEQ ID NO 97
<211> LENGTH: 7
<212> TYPE: PRT
<213> ORGANISM: Homo sapiens

<400> SEQUENCE: 97

Lys Val Ser His Arg Phe Ser
1               5

<210> SEQ ID NO 98
<211> LENGTH: 7
<212> TYPE: PRT
<213> ORGANISM: Homo sapiens

<400> SEQUENCE: 98

Tyr Thr Ser Thr Leu Arg Pro
1               5

<210> SEQ ID NO 99
<211> LENGTH: 7
<212> TYPE: PRT
<213> ORGANISM: Homo sapiens

<400> SEQUENCE: 99

Ser Ala Ser Tyr Arg Tyr Asn
1               5

<210> SEQ ID NO 100
<211> LENGTH: 7
<212> TYPE: PRT
<213> ORGANISM: Homo sapiens

<400> SEQUENCE: 100

Trp Ala Ser Thr Arg Glu Ser
1               5

<210> SEQ ID NO 101
<211> LENGTH: 7
<212> TYPE: PRT
<213> ORGANISM: Homo sapiens

<400> SEQUENCE: 101

Ala Ala Thr Ser Leu Ala Asp
1               5

<210> SEQ ID NO 102
<211> LENGTH: 7
<212> TYPE: PRT
<213> ORGANISM: Homo sapiens

<400> SEQUENCE: 102

Lys Ile Ser Asn Arg Phe Phe
1               5

<210> SEQ ID NO 103
<211> LENGTH: 7
<212> TYPE: PRT
<213> ORGANISM: Homo sapiens

<400> SEQUENCE: 103

Trp Ala Ser Thr Arg Asp Ser
1               5

```
<210> SEQ ID NO 104
<211> LENGTH: 7
<212> TYPE: PRT
<213> ORGANISM: Homo sapiens

<400> SEQUENCE: 104

Ser Ala Ser Tyr Arg Tyr Asn
1               5

<210> SEQ ID NO 105
<211> LENGTH: 7
<212> TYPE: PRT
<213> ORGANISM: Homo sapiens

<400> SEQUENCE: 105

Trp Ala Ser Thr Arg Glu Ser
1               5

<210> SEQ ID NO 106
<211> LENGTH: 7
<212> TYPE: PRT
<213> ORGANISM: Homo sapiens

<400> SEQUENCE: 106

Trp Ala Ser Thr Arg Glu Thr
1               5

<210> SEQ ID NO 107
<211> LENGTH: 7
<212> TYPE: PRT
<213> ORGANISM: Homo sapiens

<400> SEQUENCE: 107

Lys Ala Ser Asn Leu His Thr
1               5

<210> SEQ ID NO 108
<211> LENGTH: 7
<212> TYPE: PRT
<213> ORGANISM: Homo sapiens

<400> SEQUENCE: 108

Lys Ala Ser Asn Leu His Thr
1               5

<210> SEQ ID NO 109
<211> LENGTH: 7
<212> TYPE: PRT
<213> ORGANISM: Homo sapiens

<400> SEQUENCE: 109

His Thr Ser Ser Leu His Ser
1               5

<210> SEQ ID NO 110
<211> LENGTH: 7
<212> TYPE: PRT
<213> ORGANISM: Homo sapiens

<400> SEQUENCE: 110

Lys Ala Ser Asn Leu His Thr
1               5
```

-continued

```
<210> SEQ ID NO 111
<211> LENGTH: 7
<212> TYPE: PRT
<213> ORGANISM: Homo sapiens

<400> SEQUENCE: 111

Trp Ala Ser Thr Arg Glu Ser
1               5

<210> SEQ ID NO 112
<211> LENGTH: 7
<212> TYPE: PRT
<213> ORGANISM: Homo sapiens

<400> SEQUENCE: 112

Ala Ala Ser Asn Gln Gly Ser
1               5

<210> SEQ ID NO 113
<211> LENGTH: 7
<212> TYPE: PRT
<213> ORGANISM: Homo sapiens

<400> SEQUENCE: 113

Ser Ala Phe Phe Arg Tyr Pro
1               5

<210> SEQ ID NO 114
<211> LENGTH: 7
<212> TYPE: PRT
<213> ORGANISM: Homo sapiens

<400> SEQUENCE: 114

Trp Ala Ser Thr Arg Glu Ser
1               5

<210> SEQ ID NO 115
<211> LENGTH: 7
<212> TYPE: PRT
<213> ORGANISM: Homo sapiens

<400> SEQUENCE: 115

Asn Val Lys Thr Leu Thr Asp
1               5

<210> SEQ ID NO 116
<211> LENGTH: 8
<212> TYPE: PRT
<213> ORGANISM: Homo sapiens

<400> SEQUENCE: 116

His Gln Tyr Leu Ser Ser Tyr Thr
1               5

<210> SEQ ID NO 117
<211> LENGTH: 9
<212> TYPE: PRT
<213> ORGANISM: Homo sapiens

<400> SEQUENCE: 117

Gln Gln Tyr Ser Lys Phe Pro Leu Thr
1               5
```

```
<210> SEQ ID NO 118
<211> LENGTH: 9
<212> TYPE: PRT
<213> ORGANISM: Homo sapiens

<400> SEQUENCE: 118

Gln Gln Tyr Ser Lys Phe Pro Leu Thr
1               5

<210> SEQ ID NO 119
<211> LENGTH: 8
<212> TYPE: PRT
<213> ORGANISM: Homo sapiens

<400> SEQUENCE: 119

Leu Gln Tyr Asp Asn Leu Trp Thr
1               5

<210> SEQ ID NO 120
<211> LENGTH: 9
<212> TYPE: PRT
<213> ORGANISM: Homo sapiens

<400> SEQUENCE: 120

Phe Gln Gly Ser His Val Pro Tyr Thr
1               5

<210> SEQ ID NO 121
<211> LENGTH: 8
<212> TYPE: PRT
<213> ORGANISM: Homo sapiens

<400> SEQUENCE: 121

Leu Gln Tyr Asp Asn Leu Trp Thr
1               5

<210> SEQ ID NO 122
<211> LENGTH: 9
<212> TYPE: PRT
<213> ORGANISM: Homo sapiens

<400> SEQUENCE: 122

Gln Gln Tyr Asn Thr Tyr Pro Trp Thr
1               5

<210> SEQ ID NO 123
<211> LENGTH: 8
<212> TYPE: PRT
<213> ORGANISM: Homo sapiens

<400> SEQUENCE: 123

Lys Gln Ser Tyr Thr Leu Arg Thr
1               5

<210> SEQ ID NO 124
<211> LENGTH: 9
<212> TYPE: PRT
<213> ORGANISM: Homo sapiens

<400> SEQUENCE: 124

Gln Gln Leu Tyr Ser Thr Pro Trp Thr
1               5
```

```
<210> SEQ ID NO 125
<211> LENGTH: 9
<212> TYPE: PRT
<213> ORGANISM: Homo sapiens

<400> SEQUENCE: 125

Phe Gln Gly Ser His Val Pro Tyr Thr
1               5

<210> SEQ ID NO 126
<211> LENGTH: 8
<212> TYPE: PRT
<213> ORGANISM: Homo sapiens

<400> SEQUENCE: 126

Lys Gln Ser Tyr Asn Leu Tyr Thr
1               5

<210> SEQ ID NO 127
<211> LENGTH: 9
<212> TYPE: PRT
<213> ORGANISM: Homo sapiens

<400> SEQUENCE: 127

Gln Gln Tyr Asn Asn Tyr Pro Tyr Thr
1               5

<210> SEQ ID NO 128
<211> LENGTH: 9
<212> TYPE: PRT
<213> ORGANISM: Homo sapiens

<400> SEQUENCE: 128

Gln Ser Asp Tyr Ser Tyr Pro Leu Thr
1               5

<210> SEQ ID NO 129
<211> LENGTH: 8
<212> TYPE: PRT
<213> ORGANISM: Homo sapiens

<400> SEQUENCE: 129

Met Gln Ser Tyr Asn Leu Arg Thr
1               5

<210> SEQ ID NO 130
<211> LENGTH: 9
<212> TYPE: PRT
<213> ORGANISM: Homo sapiens

<400> SEQUENCE: 130

Gln Gln Gly Gln Ser Trp Pro Leu Thr
1               5

<210> SEQ ID NO 131
<211> LENGTH: 9
<212> TYPE: PRT
<213> ORGANISM: Homo sapiens

<400> SEQUENCE: 131

Gln Gln Gly Gln Ser Tyr Pro Leu Thr
1               5
```

```
<210> SEQ ID NO 132
<211> LENGTH: 9
<212> TYPE: PRT
<213> ORGANISM: Homo sapiens

<400> SEQUENCE: 132

Gln Tyr Tyr Ser Lys Asp Leu Leu Thr
1               5

<210> SEQ ID NO 133
<211> LENGTH: 9
<212> TYPE: PRT
<213> ORGANISM: Homo sapiens

<400> SEQUENCE: 133

Gln Gln Gly Gln Ser Trp Pro Leu Thr
1               5

<210> SEQ ID NO 134
<211> LENGTH: 8
<212> TYPE: PRT
<213> ORGANISM: Homo sapiens

<400> SEQUENCE: 134

His Gln Tyr Leu Ser Ser Tyr Thr
1               5

<210> SEQ ID NO 135
<211> LENGTH: 9
<212> TYPE: PRT
<213> ORGANISM: Homo sapiens

<400> SEQUENCE: 135

Gln Gln Thr Lys Glu Val Pro Trp Thr
1               5

<210> SEQ ID NO 136
<211> LENGTH: 9
<212> TYPE: PRT
<213> ORGANISM: Homo sapiens

<400> SEQUENCE: 136

Gln Gln Asp Tyr Ser Ser Pro Leu Thr
1               5

<210> SEQ ID NO 137
<211> LENGTH: 8
<212> TYPE: PRT
<213> ORGANISM: Homo sapiens

<400> SEQUENCE: 137

Met Gln Ser Phe Asn Leu Arg Thr
1               5

<210> SEQ ID NO 138
<211> LENGTH: 9
<212> TYPE: PRT
<213> ORGANISM: Homo sapiens

<400> SEQUENCE: 138

Gln Gln Phe Trp Ser Ile Pro Trp Thr
1               5
```